(12) United States Patent
Li et al.

(10) Patent No.: US 9,909,112 B2
(45) Date of Patent: Mar. 6, 2018

(54) POLYPEPTIDES HAVING ALPHA-AMYLASE ACTIVITY AND POLYNUCLEOTIDES ENCODING SAME

(71) Applicant: NOVOZYMES A/S, Bagsvaerd (DK)

(72) Inventors: Ming Li, Beijing (CN); Junxin Duan, Beijing (CN); Noriko Tsutsumi, Ichikawa (JP); Guillermo Coward-Kelly, Wake Forest, NC (US); Henrik Lundkvist, Malmo (SE)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 15/587,576

(22) Filed: May 5, 2017

(65) Prior Publication Data
US 2017/0240873 A1 Aug. 24, 2017

Related U.S. Application Data

(62) Division of application No. 14/348,433, filed as application No. PCT/CN2012/082436 on Sep. 29, 2012, now abandoned.

(60) Provisional application No. 61/553,394, filed on Oct. 31, 2011.

(30) Foreign Application Priority Data

Sep. 30, 2011 (WO) ................ PCT/CN2011/080465

(51) Int. Cl.
C12N 9/30 (2006.01)
C12N 1/00 (2006.01)
C12N 1/15 (2006.01)
C12N 1/19 (2006.01)
C12P 7/14 (2006.01)
A21D 8/04 (2006.01)

(52) U.S. Cl.
CPC ............. *C12N 9/242* (2013.01); *A21D 8/042* (2013.01); *C12P 7/14* (2013.01); *C12Y 302/01001* (2013.01)

(58) Field of Classification Search
None
See application file for complete search history.

(56) References Cited

FOREIGN PATENT DOCUMENTS

| WO | 2003/012071 A2 | 2/2003 |
| WO | 2003/016535 A2 | 2/2003 |
| WO | 2006/066579 A1 | 6/2006 |
| WO | 2006/069290 A2 | 6/2006 |
| WO | 2010/091221 A1 | 8/2010 |

OTHER PUBLICATIONS

Van den Berg et al.—Genbank Access No. XP-002560482 (2009).
Van den Berg et al.—Genbank Access No. XP-002560950 (2009).
Fedorova et al.—Uniprot Access No. A1CYB1 (2007).
Payne et al.—Uniprot Acces No. B8N2R4 (2009).
Jiang et al.—GENESEQP: ABB80178 (2003).
Van Den Berg et al, 2008—Uniport Access No. B6H6W6, Nov. 2014.
WO 2006-089107 A1—Geneseq Access No. AEK44865, Aug. 2006.
WO 2008-046855—Geneseq Access No. ARN15325, Apr. 2008.
WO 2008-046855—Geneseq Access No. ARN15327, Apr. 2008.
WO 2003-012071—EBI Access No. ABQ80348, Feb. 2003.

*Primary Examiner* — David Steadman
(74) *Attorney, Agent, or Firm* — David Fazzolare

(57) ABSTRACT

The present invention relates to isolated polypeptides having alpha-amylase activity, catalytic domains, carbohydrate binding domains and polynucleotides encoding the polypeptides, catalytic domains or carbohydrate binding domains. The invention also relates to nucleic acid constructs, vectors, and host cells comprising the polynucleotides as well as methods of producing and using the polypeptides, catalytic domains or carbohydrate binding domains.

14 Claims, 1 Drawing Sheet

SEQUENCE LISTING

```
<160> NUMBER OF SEQ ID NOS: 8

<210> SEQ ID NO 1
<211> LENGTH: 1587
<212> TYPE: DNA
<213> ORGANISM: Penicillium oxalicum
<220> FEATURE:
<221> NAME/KEY: sig_peptide
<222> LOCATION: (1)..(75)
<220> FEATURE:
<221> NAME/KEY: exon
<222> LOCATION: (1)..(1011)
<220> FEATURE:
<221> NAME/KEY: exon
<222> LOCATION: (1081)..(1584)

<400> SEQUENCE: 1 atg ttc ttc aca tcc tcg gtc tgc tgg gcg gca ggc ctc acc acc ctg      48
Met Phe Phe Thr Ser Ser Val Cys Trp Ala Ala Gly Leu Thr Thr Leu
1               5                   10                  15 tca tgc ctg ctg aac ccg gtt ctc gcc gcg gac atg gct gca tgg aag      96
Ser Cys Leu Leu Asn Pro Val Leu Ala Ala Asp Met Ala Ala Trp Lys
            20                  25                  30 act cga tcc gtg tac caa acc atg acc gat cgg ttc gct cgc ccg gac     144
Thr Arg Ser Val Tyr Gln Thr Met Thr Asp Arg Phe Ala Arg Pro Asp
        35                  40                  45 ggg tcg atg acg gct ccg tgc aac gcc tcc gcg ggc ctt tac tgc gga     192
Gly Ser Met Thr Ala Pro Cys Asn Ala Ser Ala Gly Leu Tyr Cys Gly
    50                  55                  60 gga acg tgg aag ggg aca atg aat aag ttg gat tat att cag gac atg     240
Gly Thr Trp Lys Gly Thr Met Asn Lys Leu Asp Tyr Ile Gln Asp Met
65                  70                  75                  80 gga ttc gac gcg atc atg atc tcc ccg atc gta aag aac atc gag ggt     288
Gly Phe Asp Ala Ile Met Ile Ser Pro Ile Val Lys Asn Ile Glu Gly
                85                  90                  95 cgg gtc tgg tat ggt gaa gcc tat cac ggg tac tgg cca cag gat atg     336
Arg Val Trp Tyr Gly Glu Ala Tyr His Gly Tyr Trp Pro Gln Asp Met
            100                 105                 110 tac caa ctc aac cct cac ttt ggc acc gag caa gag ttg cat gat ctc     384
Tyr Gln Leu Asn Pro His Phe Gly Thr Glu Gln Glu Leu His Asp Leu
        115                 120                 125 gtc gat gcc att cat gcg cgc ggc atg tat atc ctc ttg gac agc gtc     432
Val Asp Ala Ile His Ala Arg Gly Met Tyr Ile Leu Leu Asp Ser Val
    130                 135                 140 att aac aac atg gcc tgg atg acc cgc ggc cag aac ccg gcg acg cac     480
Ile Asn Asn Met Ala Trp Met Thr Arg Gly Gln Asn Pro Ala Thr His
145                 150                 155                 160 atc gac tat tcc gcc ttg acc ccg ttc aac aac cag cag tac tat cac     528
Ile Asp Tyr Ser Ala Leu Thr Pro Phe Asn Asn Gln Gln Tyr Tyr His
```

|  |  |  |  |  |  |  |  |  |  |  |  |  |  |  |  |
|---|---|---|---|---|---|---|---|---|---|---|---|---|---|---|---|
| | | | 165 | | | | 170 | | | | 175 | | | | |
| cca | tac | tgc | aag | atc | aag | aat | tgg | aac | aac | tac | acg | gat | gcc | caa | ctg | 576 |
| Pro | Tyr | Cys | Lys | Ile | Lys | Asn | Trp | Asn | Asn | Tyr | Thr | Asp | Ala | Gln | Leu |
| | | | 180 | | | | 185 | | | | 190 | | | | |

(Segments continue with amino acid and nucleotide sequences as shown.)

```
                    165                 170                 175
cca tac tgc aag atc aag aat tgg aac aac tac acg gat gcc caa ctg     576
Pro Tyr Cys Lys Ile Lys Asn Trp Asn Asn Tyr Thr Asp Ala Gln Leu
            180                 185                 190 tgc caa aca gga gac gac cag gtc gcc ttg ccc gat ctg ttt acc gaa     624
Cys Gln Thr Gly Asp Asp Gln Val Ala Leu Pro Asp Leu Phe Thr Glu
        195                 200                 205 cat gag gac gtt cag aag aca ttg gag gac tgg gca acc gac gtg atc     672
His Glu Asp Val Gln Lys Thr Leu Glu Asp Trp Ala Thr Asp Val Ile
    210                 215                 220 aag aaa tat aac atc gac ggc ctt cga ctc gat gcg gtc aag agt ttg     720
Lys Lys Tyr Asn Ile Asp Gly Leu Arg Leu Asp Ala Val Lys Ser Leu
225                 230                 235                 240 aca ccg agc ttc ctg gcc aag ttt gtc aag aac gtc gga ggc ttc atg     768
Thr Pro Ser Phe Leu Ala Lys Phe Val Lys Asn Val Gly Gly Phe Met
                245                 250                 255 acc gga gaa cag ttc gaa aga gac tcc aag atc atc tgc gac tgg caa     816
Thr Gly Glu Gln Phe Glu Arg Asp Ser Lys Ile Ile Cys Asp Trp Gln
            260                 265                 270 aag aac tat atc tcc agc atg ccc aac tac ccc atg tac tat tcc atg     864
Lys Asn Tyr Ile Ser Ser Met Pro Asn Tyr Pro Met Tyr Tyr Ser Met
        275                 280                 285 gtc gag gcc ttt acc cag gga aac atg tca gat ctc gct gtc caa att     912
Val Glu Ala Phe Thr Gln Gly Asn Met Ser Asp Leu Ala Val Gln Ile
    290                 295                 300 gag acg atg aag tcg ctt tgt gcg gac gtg aca gag atg gtc tcc ttc     960
Glu Thr Met Lys Ser Leu Cys Ala Asp Val Thr Glu Met Val Ser Phe
305                 310                 315                 320 tca gaa aat cac gat att gct cgc gtt cgt gcg ctg agg gac gat ctc    1008
Ser Glu Asn His Asp Ile Ala Arg Val Arg Ala Leu Arg Asp Asp Leu
                325                 330                 335 tcg gtatgtataa tcctatggtc cccagcagtg aatgatcact gaccgagtct         1061
Ser ctctcttccc ccgacgcag att gcc aaa acc ttc ctc acg ttc acg tta ctg   1113
               Ile Ala Lys Thr Phe Leu Thr Phe Thr Leu Leu
                       340                 345 ttc gac gga atc ccc atg ctc tat cag ggc caa gaa cag ttc ttg gac    1161
Phe Asp Gly Ile Pro Met Leu Tyr Gln Gly Gln Glu Gln Phe Leu Asp
350                 355                 360 ggg ttg tct agt ccc gag aat cgt caa gcg atc tgg ctc acg ggc tac    1209
Gly Leu Ser Ser Pro Glu Asn Arg Gln Ala Ile Trp Leu Thr Gly Tyr
365                 370                 375                 380 aac tcc aac gcg ccc ctc tac cag ctc acc aag gcc ctc aac agc ctt    1257
Asn Ser Asn Ala Pro Leu Tyr Gln Leu Thr Lys Ala Leu Asn Ser Leu
            385                 390                 395 cgg cgc cat gcc ctt gag ctg gat ccc aac tac gtc aac atc cca acc    1305
Arg Arg His Ala Leu Glu Leu Asp Pro Asn Tyr Val Asn Ile Pro Thr
        400                 405                 410 tac ccc atc tat cgg ggt gcc agt gag att gcg gtc agt aag ggt gtg    1353
Tyr Pro Ile Tyr Arg Gly Ala Ser Glu Ile Ala Val Ser Lys Gly Val
    415                 420                 425 cag ggt cga cag gtc gtc acc gtc gtc acc aat caa ggc gtc aag ggt    1401
Gln Gly Arg Gln Val Val Thr Val Val Thr Asn Gln Gly Val Lys Gly
430                 435                 440 ggc tcc tac acg ctc acc ttg ccc gcg tcc ttc aac gcg atg acg ccc    1449
Gly Ser Tyr Thr Leu Thr Leu Pro Ala Ser Phe Asn Ala Met Thr Pro
445                 450                 455                 460 gtg acg gag atc atc acc tgt tcg aat tac acg gtc gat gcc cgg gga    1497
Val Thr Glu Ile Ile Thr Cys Ser Asn Tyr Thr Val Asp Ala Arg Gly
```

```
                465                 470                 475
tcg ctg gtc gtg cag atg gac aaa gga gag cct cgg gtc ttc ttc ccg   1545
Ser Leu Val Val Gln Met Asp Lys Gly Glu Pro Arg Val Phe Phe Pro
            480                 485                 490 aca cag ttg atg gaa ggc agc gga ttg tgt ggt tat tcc taa           1587
Thr Gln Leu Met Glu Gly Ser Gly Leu Cys Gly Tyr Ser
        495                 500                 505

<210> SEQ ID NO 2
<211> LENGTH: 505
<212> TYPE: PRT
<213> ORGANISM: Penicillium oxalicum

<400> SEQUENCE: 2

Met Phe Phe Thr Ser Ser Val Cys Trp Ala Ala Gly Leu Thr Thr Leu
1               5                   10                  15

Ser Cys Leu Leu Asn Pro Val Leu Ala Ala Asp Met Ala Ala Trp Lys
            20                  25                  30

Thr Arg Ser Val Tyr Gln Thr Met Thr Asp Arg Phe Ala Arg Pro Asp
        35                  40                  45

Gly Ser Met Thr Ala Pro Cys Asn Ala Ser Ala Gly Leu Tyr Cys Gly
    50                  55                  60

Gly Thr Trp Lys Gly Thr Met Asn Lys Leu Asp Tyr Ile Gln Asp Met
65                  70                  75                  80

Gly Phe Asp Ala Ile Met Ile Ser Pro Ile Val Lys Asn Ile Glu Gly
                85                  90                  95

Arg Val Trp Tyr Gly Glu Ala Tyr His Gly Tyr Trp Pro Gln Asp Met
            100                 105                 110

Tyr Gln Leu Asn Pro His Phe Gly Thr Glu Gln Glu Leu His Asp Leu
        115                 120                 125

Val Asp Ala Ile His Ala Arg Gly Met Tyr Ile Leu Leu Asp Ser Val
    130                 135                 140

Ile Asn Asn Met Ala Trp Met Thr Arg Gly Gln Asn Pro Ala Thr His
145                 150                 155                 160

Ile Asp Tyr Ser Ala Leu Thr Pro Phe Asn Asn Gln Gln Tyr Tyr His
                165                 170                 175

Pro Tyr Cys Lys Ile Lys Asn Trp Asn Asn Tyr Thr Asp Ala Gln Leu
            180                 185                 190

Cys Gln Thr Gly Asp Asp Gln Val Ala Leu Pro Asp Leu Phe Thr Glu
        195                 200                 205

His Glu Asp Val Gln Lys Thr Leu Glu Asp Trp Ala Thr Asp Val Ile
    210                 215                 220

Lys Lys Tyr Asn Ile Asp Gly Leu Arg Leu Asp Ala Val Lys Ser Leu
225                 230                 235                 240

Thr Pro Ser Phe Leu Ala Lys Phe Val Lys Asn Val Gly Gly Phe Met
                245                 250                 255

Thr Gly Glu Gln Phe Glu Arg Asp Ser Lys Ile Ile Cys Asp Trp Gln
            260                 265                 270

Lys Asn Tyr Ile Ser Ser Met Pro Asn Tyr Pro Met Tyr Tyr Ser Met
        275                 280                 285

Val Glu Ala Phe Thr Gln Gly Asn Met Ser Asp Leu Ala Val Gln Ile
    290                 295                 300

Glu Thr Met Lys Ser Leu Cys Ala Asp Val Thr Glu Met Val Ser Phe
305                 310                 315                 320

Ser Glu Asn His Asp Ile Ala Arg Val Arg Ala Leu Arg Asp Asp Leu
```

```
                    325                 330                 335
Ser Ile Ala Lys Thr Phe Leu Thr Phe Thr Leu Leu Phe Asp Gly Ile
            340                 345                 350

Pro Met Leu Tyr Gln Gly Gln Glu Gln Phe Leu Asp Gly Leu Ser Ser
            355                 360                 365

Pro Glu Asn Arg Gln Ala Ile Trp Leu Thr Gly Tyr Asn Ser Asn Ala
            370                 375                 380

Pro Leu Tyr Gln Leu Thr Lys Ala Leu Asn Ser Leu Arg Arg His Ala
385                 390                 395                 400

Leu Glu Leu Asp Pro Asn Tyr Val Asn Ile Pro Thr Tyr Pro Ile Tyr
                405                 410                 415

Arg Gly Ala Ser Glu Ile Ala Val Ser Lys Gly Val Gln Gly Arg Gln
            420                 425                 430

Val Val Thr Val Thr Asn Gln Gly Val Lys Gly Ser Tyr Thr
            435                 440                 445

Leu Thr Leu Pro Ala Ser Phe Asn Ala Met Thr Pro Val Thr Glu Ile
        450                 455                 460

Ile Thr Cys Ser Asn Tyr Thr Val Asp Ala Arg Gly Ser Leu Val Val
465                 470                 475                 480

Gln Met Asp Lys Gly Glu Pro Arg Val Phe Pro Thr Gln Leu Met
                485                 490                 495

Glu Gly Ser Gly Leu Cys Gly Tyr Ser
            500                 505

<210> SEQ ID NO 3
<211> LENGTH: 2354
<212> TYPE: DNA
<213> ORGANISM: Penicillium oxalicum
<220> FEATURE:
<221> NAME/KEY: sig_peptide
<222> LOCATION: (1)..(60)
<220> FEATURE:
<221> NAME/KEY: exon
<222> LOCATION: (1)..(156)
<220> FEATURE:
<221> NAME/KEY: exon
<222> LOCATION: (235)..(273)
<220> FEATURE:
<221> NAME/KEY: exon
<222> LOCATION: (335)..(450)
<220> FEATURE:
<221> NAME/KEY: exon
<222> LOCATION: (503)..(611)
<220> FEATURE:
<221> NAME/KEY: exon
<222> LOCATION: (671)..(899)
<220> FEATURE:
<221> NAME/KEY: exon
<222> LOCATION: (962)..(1124)
<220> FEATURE:
<221> NAME/KEY: exon
<222> LOCATION: (1173)..(1319)
<220> FEATURE:
<221> NAME/KEY: exon
<222> LOCATION: (1375)..(1615)
<220> FEATURE:
<221> NAME/KEY: exon
<222> LOCATION: (1695)..(2354)

<400> SEQUENCE: 3 atg aaa ttc ctt gga cta gct gct ttg ttt ctt gcc cag acc gtg gcg     48
Met Lys Phe Leu Gly Leu Ala Ala Leu Phe Leu Ala Gln Thr Val Ala
1               5                   10                  15 ggt ctg acg gct gcc caa tgg cgc agc caa tcg atc tac ttc ctc atg     96
Gly Leu Thr Ala Ala Gln Trp Arg Ser Gln Ser Ile Tyr Phe Leu Met
```

```
                20              25              30
act gat cgg ttt ggt cga acc gac aag tcc gtg act gcc cca tgc aac    144
Thr Asp Arg Phe Gly Arg Thr Asp Lys Ser Val Thr Ala Pro Cys Asn
         35              40              45 aca aat gac cga gtaagttctc cccccttttt cgcgtcgggg ggtggttcaa         196
Thr Asn Asp Arg
 50 aacttttgtc gtctgtggta ctgattgaat tctccaag gta tac tgt ggt gga act  252
                                          Val Tyr Cys Gly Gly Thr
                                                           55 tgg caa ggc att atc aat caa gtgagatgca tccgcagccc atggataagg       303
Trp Gln Gly Ile Ile Asn Gln
 60                      65 taaacaatct aggttctgac gtagcttcaa g ttg gat tac atc caa gga atg     355
                                  Leu Asp Tyr Ile Gln Gly Met
                                                           70 gga ttt act gcg att tgg atc act cca gtc aca gag cag ctc cct caa    403
Gly Phe Thr Ala Ile Trp Ile Thr Pro Val Thr Glu Gln Leu Pro Gln
         75              80              85 gat act ggg gac ggt gaa gca tac cac gga tat tgg caa cag gaa at     450
Asp Thr Gly Asp Gly Glu Ala Tyr His Gly Tyr Trp Gln Gln Glu Ile
 90              95              100 gtatatgcat cttccaactt cgccccaaat cctctctgac aaggcgatac ag a tac    506
                                                           Tyr
                                                           105 aat gtc aac aac aac tac ggc act gct gcc gat ctc aag gct ctt tcg    554
Asn Val Asn Asn Asn Tyr Gly Thr Ala Ala Asp Leu Lys Ala Leu Ser
                 110             115             120 caa gcc ctt cac agt cgt gga atg tac ctc atg gtt gat gtt gtc gcg    602
Gln Ala Leu His Ser Arg Gly Met Tyr Leu Met Val Asp Val Val Ala
         125             130             135 aac cac atg gtgacttggc tctctctacg ggtgaaaacg agcaggcttc            651
Asn His Met
         140 taacttttc ggtctccag ggc tac gcg ggg gcc gga aac acc gtc gac tac    703
                   Gly Tyr Ala Gly Ala Gly Asn Thr Val Asp Tyr
                                     145             150 agt gtg ttc aag cca ttc agc tcc tct tcg tac ttc cac ccg tat tgt    751
Ser Val Phe Lys Pro Phe Ser Ser Ser Ser Tyr Phe His Pro Tyr Cys
         155             160             165 ttg atc agc gat tac tca aat cag aca aat gtc gag gac tgt tgg ctt    799
Leu Ile Ser Asp Tyr Ser Asn Gln Thr Asn Val Glu Asp Cys Trp Leu
         170             175             180 ggg gac acc acc gtc tca ctc ccc gat ctt gat acc act ctt tct tcc    847
Gly Asp Thr Thr Val Ser Leu Pro Asp Leu Asp Thr Thr Leu Ser Ser
         185             190             195 gtg cag acg atc tgg tat aat tgg gtc agt gac cta gtt tca aac tat    895
Val Gln Thr Ile Trp Tyr Asn Trp Val Ser Asp Leu Val Ser Asn Tyr
200              205             210             215 tcc a gtgagtatga cctgaaaaga ggccgtgaat tcattcagca aagcctgaca       949
Ser ttctgtaact ag tc gac ggt ctt cgg atc gat act gtc aag cac gtt caa  999
              Ile Asp Gly Leu Arg Ile Asp Thr Val Lys His Val Gln
                                 220             225 aag tca ttc tgg cct ggc tat cag agt gct gct ggt gtc tac tgt gtt   1047
Lys Ser Phe Trp Pro Gly Tyr Gln Ser Ala Ala Gly Val Tyr Cys Val
230              235             240             245 gga gag gtc ttc agt ggt gat ccg gct tac act tgc cct tat caa aac   1095
Gly Glu Val Phe Ser Gly Asp Pro Ala Tyr Thr Cys Pro Tyr Gln Asn
```

```
                250                   255                   260
tac ctt gat ggg gtt ttg aat tat cca at  gtaagccgca tctcatcaat        1144
Tyr Leu Asp Gly Val Leu Asn Tyr Pro Ile
                265                   270 tcgctggata caatctgacc agacgcag c tat tac caa tta ctc ggc gca ttt     1197
                                Tyr Tyr Gln Leu Leu Gly Ala Phe
                                                        275 aaa tca acc agt gga agc atc agc agc ctt tac aac atg atc aac tct     1245
Lys Ser Thr Ser Gly Ser Ile Ser Ser Leu Tyr Asn Met Ile Asn Ser
280                 285                 290                 295 gtt gcg tcc gac tgt gct gac cca acc ctg ctg ggt aac ttt att gaa     1293
Val Ala Ser Asp Cys Ala Asp Pro Thr Leu Leu Gly Asn Phe Ile Glu
                    300                 305                 310 aac cat gat aac cca cgc ttt gct tc  gtaagttggg atttttgcct            1339
Asn His Asp Asn Pro Arg Phe Ala Ser
                315                 320 tgcgtgtctg aactgagctc atccgcaaaa tgaag g tac aca agc gac tac tcg    1393
                                        Tyr Thr Ser Asp Tyr Ser
                                                            325 caa gcg aaa aat gtc atc tcg ttc att ttc ttg tct gat ggc att ccg     1441
Gln Ala Lys Asn Val Ile Ser Phe Ile Phe Leu Ser Asp Gly Ile Pro
                330                 335                 340 atc gtc tat gcc gga cag gaa cag cac tac agt ggc ggt aac gac cct     1489
Ile Val Tyr Ala Gly Gln Glu Gln His Tyr Ser Gly Gly Asn Asp Pro
                345                 350                 355 gct aac cgt gaa gcg act tgg ctt tcc gga tac tca aag aac gct caa     1537
Ala Asn Arg Glu Ala Thr Trp Leu Ser Gly Tyr Ser Lys Asn Ala Gln
360                 365                 370 ctg tac caa cac att gct tcg acg aac aaa atc cgc agt ctt gcg att     1585
Leu Tyr Gln His Ile Ala Ser Thr Asn Lys Ile Arg Ser Leu Ala Ile
375                 380                 385                 390 tca aag gat gcc aac tac atc act tcc aag gtgtgtgaat ggagtgcaac       1635
Ser Lys Asp Ala Asn Tyr Ile Thr Ser Lys
                395                 400 ttctctttc ttgcaaagag aaaataaagg gctggaaaaa gctaatttga cggacatag     1694 aac aat gct ttc tac act gac agt aac acc atc gcc atg aag aaa gga    1742
Asn Asn Ala Phe Tyr Thr Asp Ser Asn Thr Ile Ala Met Lys Lys Gly
                405                 410                 415 tcc tcc gga tcg cag gtc gtg aca gtt ctc tca aac cgt ggc tcg tca    1790
Ser Ser Gly Ser Gln Val Val Thr Val Leu Ser Asn Arg Gly Ser Ser
                420                 425                 430 ggt agc tcg tac act ttg agt ctc agc ggc agc ggc tat gcg gct ggc    1838
Gly Ser Ser Tyr Thr Leu Ser Leu Ser Gly Ser Gly Tyr Ala Ala Gly
                435                 440                 445 acc aag ctg gtg gaa atg tac acc tgc acc gct gtt acc gtt gat tcg    1886
Thr Lys Leu Val Glu Met Tyr Thr Cys Thr Ala Val Thr Val Asp Ser
    450                 455                 460 aat ggc aac atc gca gtt tcc atg acc tct ggg ctg cct cga gtg ttt    1934
Asn Gly Asn Ile Ala Val Ser Met Thr Ser Gly Leu Pro Arg Val Phe
465                 470                 475                 480 atg ctg gcc tcc tct gca tgc tct ctt tgc agt tcc gcg tgc tcc gca    1982
Met Leu Ala Ser Ser Ala Cys Ser Leu Cys Ser Ser Ala Cys Ser Ala
                485                 490                 495 act gca acc acg ctc aag act acg acc gct acg gcg acc agc tgc acc    2030
Thr Ala Thr Thr Leu Lys Thr Thr Thr Ala Thr Ala Thr Ser Cys Thr
                500                 505                 510 caa gcc acc gct ctg cct gtt ctg ttt aaa gat aca gtg acc act tct    2078
Gln Ala Thr Ala Leu Pro Val Leu Phe Lys Asp Thr Val Thr Thr Ser
            515                 520                 525
```

```
tac ggt cag agc gtc tat ctc gcc ggc tcg atc agt cag ctc ggt aac      2126
Tyr Gly Gln Ser Val Tyr Leu Ala Gly Ser Ile Ser Gln Leu Gly Asn
        530                 535                 540 tgg aac gcc gct aat gct gtt gcg ttg tcc gct gat aag tac aca tca      2174
Trp Asn Ala Ala Asn Ala Val Ala Leu Ser Ala Asp Lys Tyr Thr Ser
545                 550                 555                 560 tcc aat ccc tta tgg tac gca act gtg acg ctg ccc gtg gga act tcg      2222
Ser Asn Pro Leu Trp Tyr Ala Thr Val Thr Leu Pro Val Gly Thr Ser
                565                 570                 575 ttc cag tac aag ttc atc aaa aag acg agc ggc tct ggc tcg gtc act      2270
Phe Gln Tyr Lys Phe Ile Lys Lys Thr Ser Gly Ser Gly Ser Val Thr
            580                 585                 590 tgg gag agc gac ccc aac cgg tcg tac aca gtc ccc acc gga tgc gtg      2318
Trp Glu Ser Asp Pro Asn Arg Ser Tyr Thr Val Pro Thr Gly Cys Val
        595                 600                 605 ggc tct acg gcc act gtc act gct acg tgg agg tag                      2354
Gly Ser Thr Ala Thr Val Thr Ala Thr Trp Arg
                610                 615

<210> SEQ ID NO 4
<211> LENGTH: 619
<212> TYPE: PRT
<213> ORGANISM: Penicillium oxalicum

<400> SEQUENCE: 4

Met Lys Phe Leu Gly Leu Ala Ala Leu Phe Leu Ala Gln Thr Val Ala
1               5                   10                  15

Gly Leu Thr Ala Ala Gln Trp Arg Ser Gln Ser Ile Tyr Phe Leu Met
            20                  25                  30

Thr Asp Arg Phe Gly Arg Thr Asp Lys Ser Val Thr Ala Pro Cys Asn
        35                  40                  45

Thr Asn Asp Arg Val Tyr Cys Gly Gly Thr Trp Gln Gly Ile Ile Asn
    50                  55                  60

Gln Leu Asp Tyr Ile Gln Gly Met Gly Phe Thr Ala Ile Trp Ile Thr
65                  70                  75                  80

Pro Val Thr Glu Gln Leu Pro Gln Asp Thr Gly Asp Gly Glu Ala Tyr
                85                  90                  95

His Gly Tyr Trp Gln Gln Glu Ile Tyr Asn Val Asn Asn Tyr Gly
            100                 105                 110

Thr Ala Ala Asp Leu Lys Ala Leu Ser Gln Ala Leu His Ser Arg Gly
        115                 120                 125

Met Tyr Leu Met Val Asp Val Ala Asn His Met Gly Tyr Ala Gly
    130                 135                 140

Ala Gly Asn Thr Val Asp Tyr Ser Val Phe Lys Pro Phe Ser Ser Ser
145                 150                 155                 160

Ser Tyr Phe His Pro Tyr Cys Leu Ile Ser Asp Tyr Ser Asn Gln Thr
                165                 170                 175

Asn Val Glu Asp Cys Trp Leu Gly Asp Thr Thr Val Ser Leu Pro Asp
            180                 185                 190

Leu Asp Thr Thr Leu Ser Ser Val Gln Thr Ile Trp Tyr Asn Trp Val
        195                 200                 205

Ser Asp Leu Val Ser Asn Tyr Ser Ile Asp Gly Leu Arg Ile Asp Thr
    210                 215                 220

Val Lys His Val Gln Lys Ser Phe Trp Pro Gly Tyr Gln Ser Ala Ala
225                 230                 235                 240

Gly Val Tyr Cys Val Gly Glu Val Phe Ser Gly Asp Pro Ala Tyr Thr
```

```
                       245                 250                 255
Cys Pro Tyr Gln Asn Tyr Leu Asp Gly Val Leu Asn Tyr Pro Ile Tyr
            260                 265                 270
Tyr Gln Leu Leu Gly Ala Phe Lys Ser Thr Ser Gly Ser Ile Ser Ser
        275                 280                 285
Leu Tyr Asn Met Ile Asn Ser Val Ala Ser Asp Cys Ala Asp Pro Thr
    290                 295                 300
Leu Leu Gly Asn Phe Ile Glu Asn His Asp Asn Pro Arg Phe Ala Ser
305                 310                 315                 320
Tyr Thr Ser Asp Tyr Ser Gln Ala Lys Asn Val Ile Ser Phe Ile Phe
                325                 330                 335
Leu Ser Asp Gly Ile Pro Ile Val Tyr Ala Gly Gln Glu Gln His Tyr
            340                 345                 350
Ser Gly Gly Asn Asp Pro Ala Asn Arg Glu Ala Thr Trp Leu Ser Gly
        355                 360                 365
Tyr Ser Lys Asn Ala Gln Leu Tyr Gln His Ile Ala Ser Thr Asn Lys
    370                 375                 380
Ile Arg Ser Leu Ala Ile Ser Lys Asp Ala Asn Tyr Ile Thr Ser Lys
385                 390                 395                 400
Asn Asn Ala Phe Tyr Thr Asp Ser Asn Thr Ile Ala Met Lys Lys Gly
                405                 410                 415
Ser Ser Gly Ser Gln Val Val Thr Val Leu Ser Asn Arg Gly Ser Ser
            420                 425                 430
Gly Ser Ser Tyr Thr Leu Ser Leu Ser Gly Ser Gly Tyr Ala Ala Gly
        435                 440                 445
Thr Lys Leu Val Glu Met Tyr Thr Cys Thr Ala Val Thr Val Asp Ser
    450                 455                 460
Asn Gly Asn Ile Ala Val Ser Met Thr Ser Gly Leu Pro Arg Val Phe
465                 470                 475                 480
Met Leu Ala Ser Ala Cys Ser Leu Cys Ser Ser Ala Cys Ser Ala
                485                 490                 495
Thr Ala Thr Thr Leu Lys Thr Thr Thr Ala Thr Ala Thr Ser Cys Thr
            500                 505                 510
Gln Ala Thr Ala Leu Pro Val Leu Phe Lys Asp Thr Val Thr Thr Ser
        515                 520                 525
Tyr Gly Gln Ser Val Tyr Leu Ala Gly Ser Ile Ser Gln Leu Gly Asn
    530                 535                 540
Trp Asn Ala Ala Asn Ala Val Ala Leu Ser Ala Asp Lys Tyr Thr Ser
545                 550                 555                 560
Ser Asn Pro Leu Trp Tyr Ala Thr Val Thr Leu Pro Val Gly Thr Ser
                565                 570                 575
Phe Gln Tyr Lys Phe Ile Lys Lys Thr Ser Gly Ser Gly Ser Val Thr
            580                 585                 590
Trp Glu Ser Asp Pro Asn Arg Ser Tyr Thr Val Pro Thr Gly Cys Val
        595                 600                 605
Gly Ser Thr Ala Thr Val Thr Ala Thr Trp Arg
    610                 615
```

<210> SEQ ID NO 5
<211> LENGTH: 44
<212> TYPE: DNA
<213> ORGANISM: Artificial Sequence
<220> FEATURE:
<223> OTHER INFORMATION: Synthetic construct

```
<400> SEQUENCE: 5
attattcgaa ggatccacca tgttcttcac atcctcggtc tgct                          44

<210> SEQ ID NO 6
<211> LENGTH: 39
<212> TYPE: DNA
<213> ORGANISM: Artificial Sequence
<220> FEATURE:
<223> OTHER INFORMATION: Synthetic construct

<400> SEQUENCE: 6
ggtgctgatg gaattcggaa taaccacaca atccgctgc                               39

<210> SEQ ID NO 7
<211> LENGTH: 48
<212> TYPE: DNA
<213> ORGANISM: Artificial Sequence
<220> FEATURE:
<223> OTHER INFORMATION: Synthetic construct

<400> SEQUENCE: 7
attattcgaa ggatccacca tgaaattcct tggactagct gctttgtt                     48

<210> SEQ ID NO 8
<211> LENGTH: 39
<212> TYPE: DNA
<213> ORGANISM: Artificial Sequence
<220> FEATURE:
<223> OTHER INFORMATION: Synthetic construct

<400> SEQUENCE: 8
ggtgctgatg gaattccctc cacgtagcag tgacagtgg                               39
```

POLYPEPTIDES HAVING ALPHA-AMYLASE ACTIVITY AND POLYNUCLEOTIDES ENCODING SAME

CROSS-REFERENCE TO RELATED APPLICATIONS

This application is a division of U.S. Ser. No. 14/348,433 filed Mar. 28, 2014, pending, which is a 35 U.S.C. 371 national application of PCT/CN2012/082436 filed Sep. 29, 2012, which claims priority or the benefit under 35 U.S.C. 119 of International application no. PCT/CN11/080465 filed Sep. 30, 2011 and U.S. provisional application No. 61/553,394 filed Oct. 31, 2011, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having alpha-amylase activity, catalytic domains, and carbohydrate binding domains, and polynucleotides encoding the polypeptides, catalytic domains, and carbohydrate binding domains. The invention also relates to nucleic acid constructs, vectors, and host cells comprising the polynucleotides as well as methods of producing and using the polypeptides, catalytic domains, and carbohydrate binding domains.

Description of the Related Art

Alpha-amylases (alpha-1,4-glucan-4-glucanohydrolases, EC. 3.2.1.1) constitute a group of enzymes which catalyze hydrolysis of starch and other linear and branched 1,4-glucosidic oligo- and polysaccharides.

For a number of years alpha-amylase enzymes have been used for a variety of different purposes, the most important of which are starch liquefaction, textile desizing, textile washing, starch modification in the paper and pulp industry, and for brewing, ethanol production and baking.

The object of the present invention is to provide alpha-amylases for conversion of starch into maltodextrins, mono- and disaccharides and/or useful in processes involving starch liquefaction, textile washing, textile desizing, starch modification in the paper and pulp industry, and for brewing, ethanol production and baking.

A polypeptide from *Aspergillus fumigatus* having alpha-amylase activity is disclosed in WO 2003/012071 (Geneseq:ABB80178). A polypeptide from *Aspergillus terreus* having alpha-amylase activity is disclosed in WO 2010/091221. A putative alpha-amylase from *Aspergillus flavus* is disclosed in UNIPROT:B8N2R4 B8N2R4_ASPFN. A putative alpha-amylase from *Neosartorya fischeri* is disclosed in UNIPROT:A1CYB1 A1CYB1_NEOFI.

SUMMARY OF THE INVENTION

The present invention relates to isolated polypeptides having alpha-amylase activity selected from the group consisting of:

(a) a polypeptide having at least 80% sequence identity to the mature polypeptide of SEQ ID NO: 4, or at least 65% sequence identity to the mature polypeptide of SEQ ID NO: 2;

(b) a polypeptide encoded by a polynucleotide that hybridizes under low, medium, medium-high, high, or very high stringency conditions with (i) the mature polypeptide coding sequence of SEQ ID NO: 3, or the mature polypeptide coding sequence of SEQ ID NO: 1, (ii) the cDNA sequence thereof, or (iii) the full-length complement of (i) or (ii);

(c) a polypeptide encoded by a polynucleotide having at least 80% sequence identity to the mature polypeptide coding sequence of SEQ ID NO: 3, or at least 65% sequence identity to the mature polypeptide coding sequence of SEQ ID NO: 1, or the cDNA sequences thereof;

(d) a variant of the mature polypeptide of SEQ ID NO: 4 or SEQ ID NO: 2, comprising a substitution, deletion, and/or insertion at one or more (e.g., several) positions; and (e) a fragment of the polypeptide of (a), (b), (c), or (d) that has alpha-amylase activity.

The present invention also relates to isolated polypeptides comprising a catalytic domain selected from the group consisting of:

(a) a catalytic domain having at least 80% sequence identity to amino acids 21 to 493 of SEQ ID NO: 4, or at least 65% sequence identity to amino acids 26 to 503 of SEQ ID NO: 2;

(b) a catalytic domain encoded by a polynucleotide that hybridizes under low, medium, medium-high, high, or very high stringency conditions with (i) nucleotides 61 to 1973 of SEQ ID NO: 3, or nucleotides 76 to 1578 of SEQ ID NO: 1, (ii) the cDNA sequence thereof, or (iii) the full-length complement of (i) or (ii);

(c) a catalytic domain encoded by a polynucleotide having at least 80% sequence identity to nucleotides 61 to 1973 of SEQ ID NO: 3 or the cDNA thereof, or at least 65% sequence identity to nucleotides 76 to 1578 of SEQ ID NO: 1 or the cDNA thereof;

(d) a variant of amino acids 21 to 493 of SEQ ID NO: 4 comprising a substitution, deletion, and/or insertion at one or more (e.g., several) positions, or a variant of amino acids 26 to 503 of SEQ ID NO: 2 comprising a substitution, deletion, and/or insertion at one or more (e.g., several) positions; and (e) a fragment of the catalytic domain of (a), (b), (c), or (d) that has alpha-amylase activity.

The present invention also relates to isolated polypeptides comprising a carbohydrate binding domain selected from the group consisting of:

(a) a carbohydrate binding domain having at least 80% sequence identity to amino acids 511 to 619 of SEQ ID NO: 4;

(b) a carbohydrate binding domain encoded by a polynucleotide that hybridizes under low, medium, medium-high, high, or very high stringency conditions with (i) nucleotides 2025 to 2351 of SEQ ID NO: 3, (ii) the cDNA sequence thereof, or (iii) the full-length complement of (i) or (ii);

(c) a carbohydrate binding domain encoded by a polynucleotide having at least 80% sequence identity to nucleotides 2025 to 2351 of SEQ ID NO: 3, or the cDNA sequence thereof;

(d) a variant of amino acids 511 to 619 of SEQ ID NO: 4 comprising a substitution, deletion, and/or insertion at one or more (e.g., several) positions; and (e) a fragment of the carbohydrate binding domain of (a), (b), (c), or (d) that has binding activity.

The present invention also relates to isolated polynucleotides encoding the polypeptides of the present invention; nucleic acid constructs; recombinant expression vectors;

recombinant host cells comprising the polynucleotides; and methods of producing the polypeptides.

The present invention also relates to use of the present alpha-amylase for starch conversion in the food industry, starch modification in the paper and pulp industry, starch liquefaction, textile washing, textile desizing, brewing, ethanol production and/or baking.

The present invention also relates to use of the present alpha-amylase for production of ethanol in a process comprising hydrolyzing an ungelatinized starch.

The present invention also relates to a polynucleotide encoding a signal peptide comprising or consisting of amino acids 1 to 20 of SEQ ID NO: 4 or amino acids 1 to 25 of SEQ ID NO: 2, each of which is operably linked to a gene encoding a protein; nucleic acid constructs, expression vectors, and recombinant host cells comprising the polynucleotides; and methods of producing a protein.

Figure 1:
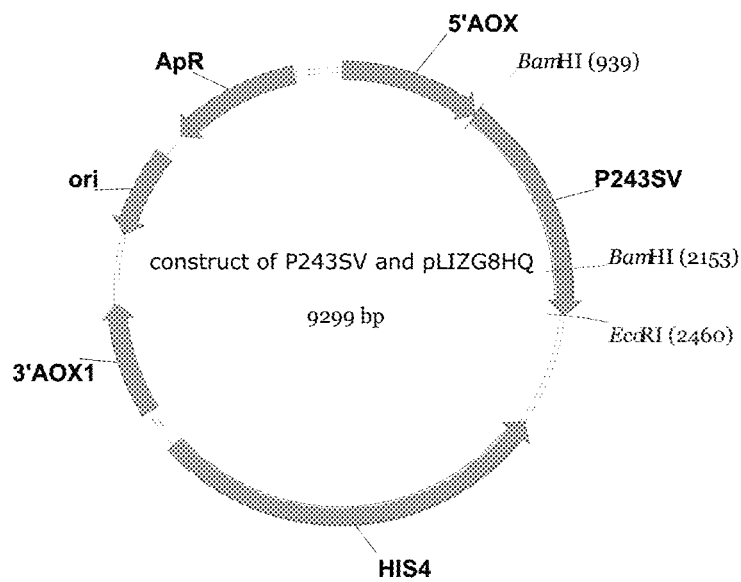
FIG. 1 shows a construct of P243SV and pLIZG8HQ.
Figure 2:
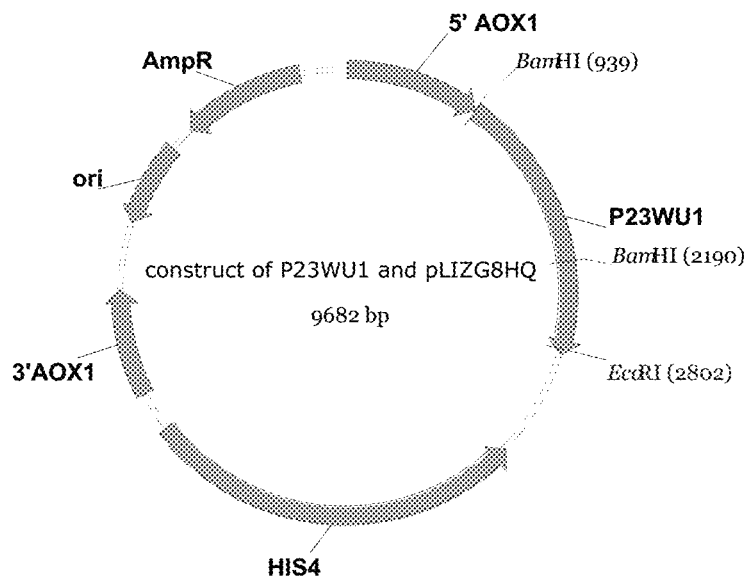
FIG. 2 shows a construct of P23WU1 and pLIZG8HQ.

DEFINITIONS alpha-amylase: The term "alpha-amylase" means an alpha-amylase activity (E.C. 3.2.1.1) that catalyzes the endohydrolysis of (1→4)-alpha-D-glucosidic linkages in polysaccharides containing three or more (1→4)-alpha-linked D-glucose units. The term "alpha-amylase activity" corresponds to the enzymes grouped in E.C. 3.2.1.1. For purposes of the present invention, alpha-amylase activity is determined according to the procedure described in the Examples. In one aspect, the polypeptides of the present invention have at least 20%, e.g., at least 40%, at least 50%, at least 60%, at least 70%, at least 80%, at least 90%, at least 95%, or at least 100% of the alpha-amylase activity of the mature polypeptide of SEQ ID NO: 2, or the mature polypeptide of SEQ ID NO: 4.

Glucoamylase activity: The term "glucoamylase (1,4-alpha-D-glucan glucohydrolase, EC 3.2.1.3) activity" is defined herein as an enzyme activity, which catalyzes the release of D-glucose from the non-reducing ends of starch or related oligo- and poly-saccharide molecules. Glucoamylase activity may be measured in AGU units.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Carbohydrate binding domain: The term "carbohydrate binding domain" or "CBD" is defined herein as an amino acid sequence comprising a CBD of family 20, also known as a starch binding domain (SBD). In SEQ ID NO: 4, amino acids 511 to 619 are the CBD.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide or a catalytic or carbohydrate binding domain having one or more (e.g., several) amino acids absent from the amino and/or carboxyl terminus of a mature polypeptide or domain; wherein the fragment has alpha-amylase or carbohydrate binding activity. In one aspect, a fragment contains at least 508 amino acid residues, preferably at least 538 amino acid residues, more preferably 568 amino acid residues of SEQ ID NO: 4. In one aspect, a fragment contains at least 407 amino acid residues, preferably at least 431 amino acid residues, more preferably 455 amino acid residues of SEQ ID NO: 2.

In one specific embodiment a fragment comprises amino acids 21 to 493 of SEQ ID NO: 4, or amino acids 26 to 503 of SEQ ID NO: 2. In one specific embodiment a fragment comprises amino acids 511 to 619 of SEQ ID NO: 4.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 21 to 619 of SEQ ID NO: 4, or amino acids 26 to 505 of SEQ ID NO: 2, based on the programs (e.g., SignalP (Nielsen et al., 1997, *Protein Engineering* 10: 1-6)) that predicts amino acids 1 to 20 of SEQ ID NO: 4, or amino acids 1 to 25 of SEQ ID NO: 2 are signal peptides. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having alpha-amylase activity. In one aspect, the mature polypeptide coding sequence is nucleotides 61 to 2351 of SEQ ID NO: 3, or nucleotides 76 to 1584 of SEQ ID NO: 1, or the cDNA sequence thereof, based on the program e.g., SignalP (Nielsen et al., 1997, supra) that predicts nucleotides 1 to 60 of SEQ ID NO: 3, or nucleotides 1 to 75 of SEQ ID NO: 1 encode a signal peptide.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having alpha-amylase activity. In one aspect, a subsequence contains at least 1524 nucleotides, preferably at least 1614 nucleotides, more preferably at least 1704 nucleotides of SEQ ID NO: 3. In one aspect, a subsequence contains at least 1221 nucleotides, preferably at least 1293 nucleotides, more preferably at least 1365 nucleotides of SEQ ID NO: 1.

Variant: The term "variant" means a polypeptide having alpha-amylase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

DETAILED DESCRIPTION OF THE INVENTION

Polypeptides Having Alpha-Amylase Activity

In an embodiment, the present invention relates to isolated polypeptides having a sequence identity to the mature polypeptide of SEQ ID NO: 4 of at least 80%, e.g., at least 85%, at least 90%, at least 91%, at least 92%, at least 93%, at least 94%, at least 95%, at least 96%, at least 97%, at least 98%, at least 99%, or 100%, which have alpha-amylase activity. In an embodiment, the present invention relates to isolated polypeptides having a sequence identity to the mature polypeptide of SEQ ID NO: 2 of at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have alpha-amylase activity.

In one aspect, the polypeptides differ by no more than 10 amino acids, e.g., 1, 2, 3, 4, 5, 6, 7, 8, 9 or 10, from the mature polypeptide of SEQ ID NO: 4 or the mature polypeptide of SEQ ID NO: 2.

A polypeptide of the present invention preferably comprises or consists of the amino acid sequence of SEQ ID NO: 4 or SEQ ID NO: 2, or an allelic variant thereof; or is a fragment thereof having alpha-amylase activity. In another aspect, the polypeptide comprises or consists of the mature polypeptide of SEQ ID NO: 4 or the mature polypeptide of SEQ ID NO: 2. In another aspect, the polypeptide comprises or consists of amino acids 21 to 619 of SEQ ID NO: 4, or amino acids 26 to 505 of SEQ ID NO: 2.

In another embodiment, the present invention relates to an isolated polypeptide having alpha-amylase activity encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 3, or the mature polypeptide coding sequence of SEQ ID NO: 1, (ii) the cDNA sequence thereof, or (iii) the full-length complement of (i) or (ii) (Sambrook et al., 1989, *Molecular Cloning, A Laboratory Manual,* 2d edition, Cold Spring Harbor, N.Y.).

The polynucleotide of SEQ ID NO: 3 or SEQ ID NO: 1 or a subsequence thereof, as well as the polypeptide of SEQ ID NO: 4 or SEQ ID NO: 2, or a fragment thereof, may be used to design nucleic acid probes to identify and clone DNA encoding polypeptides having alpha-amylase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having alpha-amylase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 3 or the mature polypeptide coding sequence thereof, or SEQ ID NO: 1 or the mature polypeptide coding sequence thereof, or a subsequence thereof, the carrier material is used in a Southern blot.

For purposes of the present invention, hybridization indicates that the polynucleotide hybridizes to a labeled nucleic acid probe corresponding to (i) SEQ ID NO: 3, or SEQ ID NO: 1; (ii) the mature polypeptide coding sequence of SEQ ID NO: 3, or SEQ ID NO: 1; (iii) the cDNA sequence thereof; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is nucleotides 61 to 2351 of SEQ ID NO: 3, or nucleotides 76 to 1584 of SEQ ID NO: 1. In another aspect, the nucleic acid probe is a polynucleotide that encodes the polypeptide of SEQ ID NO: 4, or SEQ ID NO: 2; the mature polypeptide thereof; or a fragment thereof. In another aspect, the nucleic acid probe is SEQ ID NO: 3 or SEQ ID NO: 1, or the cDNA sequence thereof.

In another embodiment, the present invention relates to an isolated polypeptide having alpha-amylase activity encoded by a polynucleotide having a sequence identity to the mature polypeptide coding sequence of SEQ ID NO: 3 or the cDNA sequence thereof of at least 80%, e.g., at least 85%, at least 90%, at least 91%, at least 92%, at least 93%, at least 94%, at least 95%, at least 96%, at least 97%, at least 98%, at least 99%, or 100%. In another embodiment, the present invention relates to an isolated polypeptide having alpha-amylase activity encoded by a polynucleotide having a sequence identity to the mature polypeptide coding sequence of SEQ ID NO: 1 or the cDNA sequence thereof of at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 4 or the mature polypeptide of SEQ ID NO: 2 comprising a substitution, deletion, and/or insertion at one or more (e.g., several) positions. In an embodiment, the number of amino acid substitutions, deletions and/or insertions introduced into the mature polypeptide of SEQ ID NO: 4 or the mature polypeptide of SEQ ID NO: 2 is at most 10, e.g., 1, 2, 3, 4, 5, 6, 7, 8, 9 or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for alpha-amylase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

In one aspect, the polypeptides having alpha-amylase activity of the present invention show very good thermostability. The polypeptides having alpha-amylase activity of the present inventions are stable at 10° C.-100° C., preferably 20° C.-80° C., more preferably 30° C.-70° C.

Sources of Polypeptides Having Alpha-Amylase Activity

A polypeptide having alpha-amylase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. In another aspect, the polypeptide is a *Penicillium* polypeptide, e.g., a polypeptide obtained from *Penicillium oxalicum*, *Penicillium funiculosum*, or *Penicillium purpurogenum*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Catalytic Domains

In one embodiment, the present invention also relates to catalytic domains having a sequence identity to amino acids 21 to 493 of SEQ ID NO: 4 of at least 80%, e.g., at least 85%, at least 90%, at least 95%, at least 96%, at least 97%, at least 98%, at least 99%, or 100%. In one embodiment, the present invention also relates to catalytic domains having a sequence identity to amino acids 26 to 503 of SEQ ID NO: 2 of at least 65%, e.g., at least 70%, at least 75%, at least 80%, at least 85%, at least 90%, at least 95%, at least 96%, at least 97%, at least 98%, at least 99%, or 100%. In one aspect, the catalytic domains comprise amino acid sequences that differ by up to 10 amino acids, e.g., 1, 2, 3, 4, 5, 6, 7, 8, 9, or 10, from amino acids 21 to 493 of SEQ ID NO: 4. In one aspect, the catalytic domains comprise amino acid sequences that differ by up to 10 amino acids, e.g., 1, 2, 3, 4, 5, 6, 7, 8, 9, or 10, from amino acids 26 to 503 of SEQ ID NO: 2.

The catalytic domain preferably comprises or consists of amino acids 21 to 493 of SEQ ID NO: 4 or amino acids 26 to 503 of SEQ ID NO: 2, or an allelic variant thereof; or is a fragment thereof having alpha-amylase activity.

In another embodiment, the present invention also relates to catalytic domains encoded by polynucleotides that hybridize under very low stringency conditions, low stringency conditions, medium stringency conditions, medium-high stringency conditions, high stringency conditions, or very high stringency conditions (as defined above) with (i) nucleotides 61 to 1973 of SEQ ID NO: 3, or nucleotides 76 to 1578 of SEQ ID NO: 1, (ii) the cDNA sequence thereof, or (iii) the full-length complement of (i) or (ii) (Sambrook et al., 1989, supra).

In another embodiment, the present invention also relates to catalytic domains encoded by polynucleotides having a sequence identity to nucleotides 61 to 1973 of SEQ ID NO: 3 of at least 80%, e.g., at least 85%, at least 90%, at least 95%, at least 96%, at least 97%, at least 98%, at least 99%, or 100%, or the cDNA sequence thereof. In another embodiment, the present invention also relates to catalytic domains encoded by polynucleotides having a sequence identity to nucleotides 76 to 1578 of SEQ ID NO: 1 of at least 65%, e.g., at least 70%, at least 75%, at least 80%, at least 85%, at least 90%, at least 95%, at least 96%, at least 97%, at least 98%, at least 99%, or 100%, or the cDNA sequence thereof.

The polynucleotide encoding the catalytic domain preferably comprises or consists of nucleotides 61 to 1973 of SEQ ID NO: 3, or nucleotides 76 to 1578 of SEQ ID NO: 1.

In another embodiment, the present invention also relates to catalytic domain variants of amino acids 21 to 493 of SEQ ID NO: 4 or amino acids 26 to 503 of SEQ ID NO: 2, is up to 10, e.g., 1, 2, 3, 4, 5, 6, 8, 9, or 10.

Binding Domains

In one embodiment, the present invention also relates to carbohydrate binding domains having a sequence identity to amino acids 511 to 619 of SEQ ID NO: 4 of at least 80%, e.g., at least 85%, at least 90%, at least 91%, at least 92%, at least 93%, at least 94%, at least 95%, at least 96%, at least 97%, at least 98%, at least 99%, or 100%. In one aspect, the carbohydrate binding domains comprise amino acid sequences that differ by up to 10 amino acids, e.g., 1, 2, 3, 4, 5, 6, 7, 8, 9, or 10, from amino acids 511 to 619 of SEQ ID NO: 4.

The carbohydrate binding domain preferably comprises or consists of amino acids 511 to 619 of SEQ ID NO: 4 or an allelic variant thereof; or is a fragment thereof having carbohydrate binding activity.

In another embodiment, the present invention also relates to carbohydrate binding domains encoded by polynucleotides that hybridize under very low stringency conditions, low stringency conditions, medium stringency conditions, medium-high stringency conditions, high stringency conditions, or very high stringency conditions (as defined above) with (i) the nucleotides 2025 to 2351 of SEQ ID NO: 3 (ii) the cDNA sequence thereof, or (iii) the full-length complement of (i) or (ii) (Sambrook et al., 1989, supra).

In another embodiment, the present invention also relates to carbohydrate binding domains encoded by polynucleotides having a sequence identity to nucleotides 2025 to 2351 of SEQ ID NO: 3 of at least 80%, e.g., at least 85%, at least 90%, at least 91%, at least 92%, at least 93%, e.g., at least 94%, at least 95%, at least 96%, at least 97%, at least 98%, at least 99%, or 100%.

The polynucleotide encoding the carbohydrate binding domain preferably comprises or consists of nucleotides 2025 to 2351 of SEQ ID NO: 3.

In another embodiment, the present invention also relates to carbohydrate binding domain variants of amino acids 511 to 619 of SEQ ID NO: 4 comprising a substitution, deletion, and/or insertion at one or more (e.g., several) positions. In one aspect, the number of amino acid substitutions, deletions and/or insertions introduced into the sequence of amino acids 511 to 619 of SEQ ID NO: 4 is up to 10, e.g., 1, 2, 3, 4, 5, 6, 8, 9, or 10.

A catalytic domain operably linked to the carbohydrate binding domain may be from an amylase, preferably an alpha-amylase, more preferably an acid alpha-amylase. The polynucleotide encoding the catalytic domain may be obtained from any prokaryotic, eukaryotic, or other source.

Polynucleotides

The present invention also relates to isolated polynucleotides encoding a polypeptide, a catalytic domain, or carbohydrate binding domain of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Penicillium* polypeptide, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, or the mature polypeptide coding sequence of SEQ ID NO: 3, or the cDNA sequence thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phospholycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are Bacillus licheniformis or Bacillus subtilis dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an Aspergillus cell are Aspergillus nidulans or Aspergillus oryzae amdS and pyrG genes and a Streptomyces hygroscopicus bar gene. Preferred for use in a Trichoderma cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in E. coli, and pUB110, pE194, pTA1060, and pAMβ1 permitting replication in Bacillus.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, Gene 98: 61-67; Cullen et al., 1987, Nucleic Acids Res. 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, Bacillus, Clostridium, Enterococcus, Geobacillus, Lactobacillus, Lactococcus, Oceanobacillus, Staphylococcus, Streptococcus, and Streptomyces. Gram-negative bacteria include, but are not limited to, Campylobacter, *E. coli*, *Flavobacterium*, *Fusobacterium*, *Helicobacter*, *Ilyobacter*, *Neisseria*, *Pseudomonas*, *Salmonella*, and *Ureaplasma*.

The bacterial host cell may be any *Bacillus* cell including, but not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida*, *Hansenula*, *Kluyveromyces*, *Pichia*, *Saccharomyces*, *Schizosaccharomyces*, or *Yarrowia* cell, such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phiebia*, *Piromyces*, *Pleurotus*, *Schizophyllum*, *Talaromyces*, *Thermoascus*, *Thielavia*, *Tolypocladium*, *Trametes*, or *Trichoderma* cell.

For example, the filamentous fungal host cell may be an *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Bjerkandera adusta*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Coprinus cinereus*, *Coriolus hirsutus*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium suiphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally (b) recovering the polypeptide. In a preferred aspect, the cell is a *Penicillium* cell. In a more preferred aspect, the cell is *Penicillium oxalicum* cell.

The present invention also relates to methods of producing a polypeptide of the present invention, comprising (a) cultivating a recombinant host cell of the present invention under conditions conducive for production of the polypeptide; and optionally (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a whole fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca*, *Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed. For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide or domain can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Removal or Reduction of Alpha-Amylase Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of the polynucleotide using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may be accomplished by insertion, substitution, or deletion of one or more nucleotides in the gene or a regulatory element required for transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In an aspect, the polynucleotide is disrupted with a selectable marker such as those described herein.

The present invention also relates to methods of inhibiting the expression of a polypeptide having alpha-amylase activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA for inhibiting transcription. In another preferred aspect, the dsRNA is micro RNA for inhibiting translation.

The present invention also relates to such double-stranded RNA (dsRNA) molecules, comprising a portion of the mature polypeptide coding sequence of SEQ ID NO: 1, or SEQ ID NO: 3 for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824; and 6,515,109.

The present invention further relates to a mutant cell of a parent cell that comprises a disruption or deletion of a polynucleotide encoding the polypeptide or a control sequence thereof or a silenced gene encoding the polypeptide, which results in the mutant cell producing less of the polypeptide or no polypeptide compared to the parent cell.

The polypeptide-deficient mutant cells are particularly useful as host cells for expression of native and heterologous polypeptides. Therefore, the present invention further relates to methods of producing a native or heterologous polypeptide, comprising (a) cultivating the mutant cell under conditions conducive for production of the polypeptide; and (b) recovering the polypeptide. The term "heterologous polypeptides" means polypeptides that are not native to the host cell, e.g., a variant of a native protein. The host cell may comprise more than one copy of a polynucleotide encoding the native or heterologous polypeptide.

The methods used for cultivation and purification of the product of interest may be performed by methods known in the art.

The methods of the present invention for producing an essentially alpha-amylase-free product is of particular interest in the production of eukaryotic polypeptides, in particular fungal proteins such as enzymes. The alpha-amylase-deficient cells may also be used to express heterologous proteins of pharmaceutical interest such as hormones, growth factors, receptors, and the like. The term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from alpha-amylase activity that is produced by a method of the present invention.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compostions may further comprise a preservative and/or anti-microbial (e.g., bacteriostatic) agent, including, but not limited to, sorbitol, sodium chloride, potassium sorbate, and others known in the art.

The fermentation broth formulations or cell compositions may further comprise multiple enzymatic activities, such as one or more (e.g., several) enzymes selected from the group comprising of; a fungal alpha-amylase (EC 3.2.1.1), a beta-amylase (E.C. 3.2.1.2), a glucoamylase (E.C.3.2.1.3), a pullulanases (E.C. 3.2.1.41), a phytase (E.C.3.1.2.28) and a protease (E.C. 3.4.). The glucoamylase may preferably be derived from a strain of *Aspergillus* sp., such as *Aspergillus niger*, or from a strain of *Talaromyces* sp. and in particular derived from *Talaromyces leycettanus* such as the glucoamylase disclosed in U.S. Pat. No. Re. 32,153, *Talaromyces duponti* and/or *Talaromyces thermopiles* such as the glucoamylases disclosed in U.S. Pat. No. 4,587,215 and more preferably derived from *Talaromyces emersonii*. Most preferably the glucoamylase is derived from *Talaromyces emersonii* strain CBS 793.97 and/or having the sequence disclosed as SEQ ID NO: 7 in WO 99/28448. Further preferred is a glucoamylase which has an amino acid sequence having at least 50%, at least 60%, at least 70%, at least 80%, at least 90%, at least 95%, at least 96%, at least 97%, at least 98%, or even at least 99% identity to the aforementioned amino acid sequence.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of preferred uses of the compositions of the present invention. The dosage of the composition and other conditions under which the composition is used may be determined on the basis of methods known in the art.

Enzyme Compositions

The present invention also relates to compositions comprising a polypeptide of the present invention. Preferably, the compositions are enriched in such a polypeptide. The term "enriched" indicates that the cellulolytic enhancing activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) enzymes selected from the group comprising of; a fungal alpha-amylase (EC 3.2.1.1), a beta-amylase (E.C. 3.2.1.2), a glucoamylase (E.C.3.2.1.3), a pullulanases (E.C. 3.2.1.41), a phytase (E.C.3.1.2.28) and a protease (E.C. 3.4.). The glucoamylase may preferably be derived from a strain of *Aspergillus* sp., such as *Aspergillus niger*, or from a strain of *Talaromyces* sp. and in particular derived from *Talaromyces leycettanus* such as the glucoamylase disclosed in U.S. Pat. No. Re. 32,153, *Talaromyces duponti* and/or *Talaromyces thermopiles* such as the glucoamylases disclosed in U.S. Pat. No. 4,587,215 and more preferably derived from *Talaromyces emersonii*. Most preferably the glucoamylase is derived from *Talaromyces emersonii* strain CBS 793.97 and/or having the sequence disclosed as SEQ ID NO: 7 in WO 99/28448. Further preferred is a glucoamylase which has an amino acid sequence having at least 50%, at least 60%, at least 70%, at least 80%, at least 90%, at least 95%, at least 96%, at least 97%, at least 98%, or even at least 99% identity to the aforementioned amino acid sequence. A commercial *Talaromyces* glucoamylase preparation is supplied by Novozymes A/S as SPIRIZYME FUEL.

Also preferred for a composition comprising the polypeptide of the present invention and a glucoamylase are polypeptides having glucoamylase activity which are derived from a strain of the genus *Trametes*, preferably *Trametes cingulate*. Further preferred is polypeptide having glucoamylase activity and having at least 50%, at least 60%, at least 70%, at least 80%, at least 90% or even at least 95% identity with amino acids for mature polypeptide of SEQ ID NO: 2 in WO 2006/069289.

Also preferred for a composition comprising the polypeptide of the present invention and a glucoamylase are polypeptides having glucoamylase activity which are derived from a strain of the genus *Pachykytospora*, preferably *Pachykytospora papyracea* or the *E. coli* strain deposited at DSMZ and given the no. DSM 17105. Further preferred are polypeptides having glucoamylase activity and having at least 50%, at least 60%, at least 70%, at least 80%, at least 90% or even at least 95% identity with amino acids for mature polypeptide of SEQ ID NO: 5 in WO 2006/069289.

The composition described above may preferably comprise acid alpha-amylase present in an amount of 0.01 to 10 AFAU/g DS, preferably 0.1 to 5 AFAU/g DS, more preferably 0.15 to 3 AFAU/g DS, and most preferably 0.3 to 2 AFAU/g DS. The dosage of the polypeptide composition of the invention and other conditions under which the composition is used may be determined on the basis of methods known in the art.

The polypeptide compositions may be prepared in accordance with methods known in the art and may be in the form of a liquid or a dry composition. For instance, the polypeptide composition may be in the form of granulate or a microgranulate. The polypeptide to be included in the composition may be stabilized in accordance with methods known in the art.

Uses

The present invention is also directed to methods for using the polypeptides having alpha-amylase activity, or compositions thereof.

The polypeptide or the composition of the present invention may be used in starch conversion, starch to sugar conversion and ethanol production etc, e.g., in liquefying and/or saccharifying a gelatinized starch or a granular starch, as well as a partly gelatinized starch. A partly gelatinized starch is a starch which to some extent is gelatinized, i.e., wherein part of the starch has irreversibly swelled and gelatinized and part of the starch is still present in a granular state. It can be used in a process for liquefying starch, wherein a gelatinized or granular starch substrate is treated in aqueous medium with the enzyme. The polypeptide or the composition of the present invention may also be used in a process for saccharification of a liquefied starch substrate. A preferred use is in a fermentation process wherein a starch substrate is liquefied and/or saccharified in the presence of the polypeptide or the composition of the present invention to produce glucose and/or maltose suitable for conversion into a fermentation product by a fermenting organism, preferably a yeast. Such fermentation processes include a process for producing ethanol for fuel or drinking ethanol (portable alcohol), a process for producing a beverage, a process for producing desired organic compounds, such as citric acid, itaconic acid, lactic acid, gluconic acid, sodium gluconate, calcium gluconate, potassium gluconate, glucono delta lactone, or sodium erythorbate; ketones; amino acids, such as glutamic acid (sodium monoglutaminate), but also more complex compounds such as antibiotics, such as penicillin, tetracyclin; enzymes; vitamins, such as riboflavin, B12, beta-carotene; hormones, which are difficult to produce synthetically.

Furthermore, due to the superior hydrolysis activity of the polypeptide of the present invention, the amount of glucoamylase during the saccharification step can be reduced. The glucoamylase may preferably be derived from a strain within *Aspergillus* sp., *Talaromyces* sp., *Pachykytospora* sp. or *Trametes* sp., more preferably from *Aspergillus niger*, *Talaromyces emersonii*, *Trametes cingulata* or *Pachykytospora papyracea*.

In a preferred embodiment, the polypeptide of the present invention is used in a process comprising fermentation to produce a fermentation product, e.g., ethanol, from a gelatinized starch. Such a process for producing ethanol from gelatinized starch by fermentation comprises: (i) liquefying the gelatinized starch with a polypeptide with alpha-amylase activity of the present invention; (ii) saccharifying the liquefied mash obtained; (iii) fermenting the material obtained in step (ii) in the presence of a fermenting organism. Optionally the process further comprises recovery of the ethanol. The saccharification and fermentation may be carried out as a simultaneous saccharification and fermentation process (SSF process).

In another preferred embodiment, the polypeptide of the present invention is used in a process comprising fermentation to produce a fermentation product, e.g., ethanol, from an ungelatinized ("raw") starch. Such a process for producing ethanol from ungelatinized starch-containing material by fermentation comprises: (i) contacting the ungelatinized starch with a polypeptide with alpha-amylase activity of the present invention to degrade the ungelatinized starch; (ii) saccharifying the mash obtained; (iii) fermenting the material obtained in step (ii) in the presence of a fermenting organism. Optionally the process further comprises recovery of the ethanol. The saccharification and fermentation may be carried out as a simultaneous saccharification and fermentation process (SSF process).

In further embodiments, the polypeptide of the present invention may also be useful in textile, fabric or garment desizing or washing, in baking, detergent and pulp and paper production.

In other aspect, the present invention provides a method of using the alpha-amylase of the present invention for producing glucose or maltose or the like from starch.

The alpha-amylases of the invention may also be used in brewing processes. Further, the alpha-amylase of the invention may be used for maltose production. High maltose syrup is typically produced as follows. To produce "High Maltose Syrup" (containing 50-55% maltose), starch is liquefied to DE 10-20. The pH and temperature of the liquefied starch is adjusted to 65° C. and to a pH around 5.0, respectively, and is subjected to maltogenic alpha-amylase activity (e.g., *Bacillus stearothermophilus* amylase, such as MALTOGENASE™ 4000 L, 0.4 l/t DS (Novozymes)), pullulanase activity (e.g., *Bacillus* pullulanase, such as PROMOZYME™ 600 L, 0.3 l/t DS (Novozymes)) and alpha-amylase activity (e.g., BAN 240 L or TERMAMYL™ 120 L, type LS, 0.4 kg/t DS (Novozymes)) for 24-41 hours. The specific process time depends on the desired saccharide spectrum to be achieved. By increasing the dosage of the maltogenic alpha-amylase and pullulanase the maltose content can be increased.

Alternatively, "High Maltose Syrup" may be produced by first liquefying starch to DE 10-20 and then adjusting the pH and temperature to 55° C. or higher and a pH around 5.5 or lower, and then subjecting the liquefied starch to a fungal alpha-amylase activity (e.g., *Bacillus stearothermophilus* amylase, such as FUNGAMYL™ 800 L (Novozymes)) for 22-44 hours. The dosage of fungal FUNGAMYL™ 800 L depends on the saccharification time foreseen, e.g., 200 g/t DS for 44 hours and 400 g/t DS for 22 hours. The alpha-amylases of the invention may substitute the FUNGAMYL™ 800 L in the above process, and then the temperature can be even higher, and the pH even lower, resulting in a faster conversion rate, and thus a better overall economy.

To produce "High Maltose Syrup" starch with maltose content of 55-65% starch is liquefied to DE 10-20. The temperature and pH of the liquefied starch is adjusted to 60° C. or higher, and to a pH around 6 or lower, and is subjected to maltogenic alpha-amylase activity (e.g., MALTOGENASE™ 4000 L, 0.25-1.0 l/t DS (Novozymes)), and fungal alpha-amylase activity (e.g., *Aspergillus* amylase, such as FUNGAMYL™ 800 L, 0.4-1.0 kg/t DS (Novo Nordisk) for 24-48 hours; or the alpha-amylase of the present invention for a shorter time.

Signal Peptide

The present invention also relates to an isolated polynucleotide encoding a signal peptide comprising or consisting of amino acids 1 to 20 of SEQ ID NO: 4, or amino acids 1 to 25 of SEQ ID NO: 2. The polynucleotides may further comprise a gene encoding a protein, which is operably linked to the signal peptide. The protein is preferably foreign to the signal peptide. In one aspect, the polynucleotide encoding the signal peptide is nucleotides 1 to 60 of SEQ ID NO: 3, or nucleotides 1 to 75 of SEQ ID NO: 1. The present invention also relates to nucleic acid constructs, expression vectors and recombinant host cells comprising such polynucleotides.

The present invention also relates to methods of producing a protein, comprising (a) cultivating a recombinant host cell comprising such polynucleotide; and optionally (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

The gene may be obtained from any prokaryotic, eukaryotic, or other source.

The present invention is further described by the following examples that should not be construed as limiting the scope of the invention.

EXAMPLES

Materials

Chemicals used as buffers and substrates were commercial products of at least reagent grade.

Strains

The fungal strain NN051380 was isolated from a soil sample collected from China with PDA medium at 25° C. using the dilution plate method. It was then purified by transferring a single conidium onto a YG agar plate. The strain NN051380 was identified as *Penicillium oxalicum* based on both morphological characteristics and ITS rDNA sequence.

Media

PDA medium was composed of 39 grams of potato dextrose agar and deionized water to 1 liter.

YG agar plates were composed of 5.0 g of yeast extract, 10.0 g of glucose, 20.0 g of agar, and deionized water to 1 liter.

YPG medium contained 0.4% of yeast extract, 0.1% of KH2PO4, 0.05% of MgSO$_4$.7H$_2$O, 1.5% glucose in deionized water.

YPM medium contained 1% yeast extract, 2% of peptone, and 2% of maltose in deionized water.

MD medium was composed of 1.34% YNB, $4 \times 10^{-5}$% biotin and 2% dextrose. For plates, 7.5 g agar was added to 200 ml of water autoclave, cooled to 60° C. and then 25 ml of 10×YNB, 25 ml of 10×D-glucose and 400 μl of 500× biotin were added.

BMSY was composed of 1% yeast extract, 2% peptone (Bacto), 100 mM potassium phosphate buffer, pH 6.0, 1.34% YNB, $4 \times 10^{-5}$% biotin and 1.82% Sorbitol. 10 g of yeast extract, 20 g peptone (Bacto) and 18.2 g Sorbitol were dissolved in 800 ml water and autoclaved for 20 minutes on liquid cycle. When the autoclaved medium was cooled to room temperature, 100 ml of 1 M potassium phosphate buffer (pH 6.0) and 100 ml of 10×YNB and 2 ml of 500× biotin were added.

Determination of Alpha-Amylase Activity

The activity of any acid alpha-amylase may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, i.e., acid stable alpha-amylase, an endo-alpha-amylase (1,4-alpha-D-glucan-glucano-hydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

Reaction condition: 10 microliters standard or enzyme sample, 70 microliters H$_2$O, and 80 microliters starch working solution (The final concentration was starch 0.35 g/L, Acetate buffer 50 mM pH 5.0, NaCl 0.1 M, CaCl$_2$ 3 mM) mixed and react for 2 minutes with shaking at 37° C. Add 40 microliters Iodine working solution (the final iodine concentration was 0.04 g/L) and react at 37° C. for 1 minute. Reading OD$_{590}$ (Before reading, shaking 10 seconds).

FUNGAMYL™ (available from Novozymes A/S) is used as standard.

Example 1: *Penicillium oxalicum* Genomic DNA Extraction

*Penicillium oxalicum* strain NN051380 was inoculated onto a PDA plate and incubated for 3 days at 25° C. in the darkness. Several mycelia-PDA plugs were inoculated into 500 ml shake flasks containing 100 ml of YPG medium. The flasks were incubated for 3 days at 25° C. with shaking at 160 rpm. The mycelia were collected by filtration through MIRACLOTH® (Calbiochem, La Jolla, Calif., USA) and frozen in liquid nitrogen. Frozen mycelia were ground, by a mortar and a pestle, to a fine powder, and genomic DNA was isolated using Large-Scale Column Fungal DNAout (BAOMAN BIOTECHNOLOGY, Shanghai, China) following the manufacturer's instruction.

Example 2: Genome Sequencing, Assembly and Annotation

The extracted genomic DNA samples were delivered to Beijing Genome Institute (BGI, Shenzhen, China) for genome sequencing using ILLUMINA® GA2 System (Illumina, Inc., San Diego, Calif., USA). The raw reads were assembled at BGI using program SOAPdenovo (Li et al. De novo assembly of human genomes with massively parallel short read sequencing. *Genome Res* (2010) vol. 20 (2) pp.

265-72). The assembled sequences were analyzed using standard bioinformatics methods for gene finding and functional prediction. Briefly, geneID (Parra et al., 2000, *Genome Research* 10(4):511-515) was used for gene prediction. Blastall version 2.2.10 (Altschul S F, Gish W, Miller W, Myers E W, Lipman D J (October 1990). "Basic local alignment search tool". *J Mol Biol* 215 (3): 403-410,) and HMMER version 2.1.1 were used to predict function based on structural homology. The family GH13 enzyme polypeptides were identified directly by analysis of the Blast results. Agene program (Munch K, Krogh A. Automatic generation of gene finders for eukaryotic species. *BMC Bioinformatics.* 2006; 7: 263) and SignalP program (Nielsen et al., 1997, *Protein Engineering* 10: 1-6) were used to identify starting codons. SignalP program was further used to estimate length of signal peptide. Pepstats program (Rice P, Longden I, Bleasby A: EMBOSS: The European Molecular Biology Open Software Suite. *Trends Genet.* 2000, 16(6):276-277) was used to estimate isoelectric point of proteins, and molecular weight.

Example 3: Preparation of *Penicillium oxalicum* Strain Total RNA and cDNA

Total RNA was prepared from the powdered mycelia by using RNeasy plant mini kit (QIAGEN, Cat. No. 74904). The cDNA was synthesized by following the instruction of 3' Rapid Amplifiction of cDNA End System (Invitrogen Corp., Carlsbad, Calif., USA).

Example 4: Cloning of the *Penicillium oxalicum* Alpha-Amylase Genes from cDNA Two genes, 51 (P243SV, corresponding to SEQ ID NO: 1) and S2 (P23WU1, corresponding to SEQ ID NO: 3), identified as GH13 alpha-amylase were selected for expression cloning.

Based on the DNA information obtained from genome sequencing, oligonucleotide primers, shown below in table 1, were designed to amplify all from cDNA of *Penicillium oxalicum*. Primers fabricated by Invitrogen (Invitrogen, Beijing, China).

TABLE 1

Primers

| Primers | Sequence (5'-3') |
|---|---|
| S1_forward (SEQ ID NO: 5) | ATTATTCGAAGGATCCACC atgttcttcacatcctcggtctgct |
| S1_reverse (SEQ ID NO: 6) | GGTGCTGATGGAATTC ggaataaccacacaatccgctgc |
| S2_forward (SEQ ID NO: 7) | ATTATTCGAAGGATCCACC atgaaattccttggactagctgctttgtt |
| S2_reverse (SEQ ID NO: 8) | GGTGCTGATGGAATTC cctccacgtagcagtgacagtgg |

Lowercase characters represent the coding regions of the genes, while capitalized parts were homologous to the insertion sites of pLIZG8HQ vector. The expression vector pLIZG8HQ contained the a-factor secretion signal derived from *S. cerevisiae*, the 5'AOX1 promoter derived from *Pichia pastoris* and the 3'AOX1 alcohol oxidase1 terminator elements. Furthermore pLIZG8HQ had pBR322 derived sequences for selection and propagation in *E. coli*, and a His4 gene, which encoded an histidinol dehydrogenase derived from *Pichia pastoris* for selection of a transformant of a His mutant *Pichia* strain.

For each gene, 20 picomoles of primer pair (each of the forward and reverse) were used in a PCR reaction composed of 2 µl of *Penicillium oxalicum* cDNA, 10 µl of 5×GC Buffer, 1.5 µl of DMSO, 2.5 mM each of dATP, dTTP, dGTP, and dCTP, and 0.6 unit of PHUSION™ High-Fidelity DNA Polymerase (Finnzymes Oy, Espoo, Finland) in a final volume of 50 µl. The amplification was performed using a Peltier Thermal Cycler (M J Research Inc., South San Francisco, Calif., USA) programmed for denaturing at 98° C. for 1 minutes; 8 cycles of denaturing at 98° C. for 15 seconds, annealing at 65° C. for 30 seconds, with 1° C. decrease per cycle and elongation at 72° C. for 75 seconds; and another 24 cycles each at 98° C. for 15 seconds, 60° C. for 30 seconds and 72° C. for 75 seconds; final extension at 72° C. for 10 minutes. The heat block then went to a 4° C. soak cycle.

The PCR products were isolated by 1.0% agarose gel electrophoresis using 90 mM Tris-borate and 1 mM EDTA (TBE) buffer where a single product band at 2.0 kb of each reaction was visualized under UV light. PCR products were then purified from solution by using an illustra GFX PCR DNA and Gel Band Purification Kit (GE Healthcare, Buckinghamshire, UK) according to the manufacturer's instructions.

Plasmid pLIZG8HQ was digested with Barn I and EcoR I, isolated by 1.0% agarose gel electrophoresis using TBE buffer (Tris/Borate/EDTA buffer), and purified using an illustra GFX PCR DNA and Gel Band Purification Kit according to the manufacturer's instructions.

An In-fusion CF Dry-down Cloning Kit (Clontech Laboratories, Inc., Mountain View, Calif., USA) was used to clone the fragment directly into the expression vector pLIZG8HQ, without the need for restriction digestion and ligation.

The respective PCR products S1 and S2 were ligated to the digested vector pLIZG8HQ using an In-fusion CF Drydown PCR Cloning kit (Clontech Laboratories, Inc., Mountain View, Calif., USA) resulting in plasmids pS1 and pS2 respectively. The cloning operation was according to the manufacturer's instruction. In brief, for each ligation reaction 30 ng of pLIZG8HQ digested with Bam I and EcoR I, and 60 ng of the *Penicillium oxalicum* alpha-amylase purified PCR product were added to the reaction vial and resuspended the powder in a final volume of 10 µl with addition of deionized water. The reaction was incubated at 37° C. for 15 minutes and then 50° C. for 15 minutes. Three microliters of the reaction products were used to transform *E. coli* TOP10 competent cells (TIANGEN Biotech (Beijing) Co. Ltd., Beijing, China). *E. coli* transformants containing expression constructs were detected by colony PCR and plasmid DNA was prepared using a QIAprep Spin Miniprep Kit (QIAGEN Inc., Valencia, Calif., USA). The *Penicillium oxalicum* alpha-amylase genes inserted in pS1 and pS2 were confirmed by DNA sequencing using 3730XL DNA Analyzers (Applied Biosystems Inc, Foster City, Calif., USA).

Example 5: Expression of *Penicillium oxalicum* Alpha-Amylase Genes in *Pichia pastoris*

*Pichia pastoris* Competent Cell Preparation

The optical density (OD) of the overnight culture of *Pichia pastoris* in YPM in shaking flask was 1.0. Cells were pelleted by centrifugation at 2000 rpm, 5 mins, 4° C. Cell pellet was then suspended in YPD plus 4-(2-hydroxyethyl)-

1-piperazineethanesulfonic acid (HEPES) and Dithiothreitol (DTT) and stand at 30° C. for 15 mins. Cells were pelleted and washed with cold water and 1M sorbitol subsequently. Finally cells were suspended in small amount of 1M sorbitol and stored in 40 µl aliquots at −70° C.

Transformation of Psi and pS2 to *Pichia pastoris*

Five milligrams of plasmid DNA pS1 or pS2 were linearized with PmeI leading to insertion of the plasmid at the chromosomal 5'AOX1 locus. Linearized plasmid DNA (500 ng) was mixed with 40 µl of competent cells and stored on ice for 5 min. Cells were transferred to an ice-cold 0.2 cm electroporation cuvette. Transformation was performed using a GenePulser II (BioRad, 2000 Alfred Nobel Drive, Hercules, Calif. 94547). Parameters used were 1500 V, 50 µF and 200Ω. Immediately after pulsing, cells were suspended in 1 ml of ice cold 1 M sorbitol. The mixtures were plated on MD plates. Plates were incubated at 28° C. for 3-4 days.

Screening Clones for Expression in Small Scale

Four candidate clones from each transformation were cultured in a 3 ml scale using 24-deep well plates (Whatman, UK). Cells were grown in BMSY media for 2.5 days at 28° C. with vigorous shaking. 0.5% methanol was added to the culture to induce heterologous gene expression. Culture was continuously grown for 4 days with a daily addition of 0.5% methanol under the same growth condition. Samples of culture were taken daily during induction and stored at −20° C. for SDS-PAGE analysis and amylase activity assay.

The culture of pS1 and pS2 showed a protein band at 55 KD and 65 KD respectively visualized on SDS-PAGE and amylase activity by testing against AZCL-amylose.

Example 6: The Purification of the Alpha-Amylases of the Present Invention

The pH of culture supernatant was adjusted to 7.0 with NaOH, then filtered through a 0.45 µm filter. The solution was applied to a 30 ml Ni-sepharose High Performance column (GE Healthcare) equilibrated with 20 mM phosphate buffered saline (PBS) containing 0.3 M NaCl at pH7.0. The protein was eluted with a linear imidazole gradient (0-500 mM). Fractions from the column were analyzed for amylase activity.

Fractions with amylase activity were checked by SDS-PAGE and the pure fractions were pooled. The SDS-PAGE showed the molecular weight of P243SV was about 55 kDa and the molecular weight of P23WU1 was about 65 kDa.

Example 7: Characterization of the Alpha-Amylase of the Present Invention

These two alpha-amylases as purified in example 6 were analysed. The results were shown in table 2 and table 3, respectively.

TABLE 2

The analytical result of P243SV

| Analysis | Entire Protein |
|---|---|
| Length | 505 aa |
| Molecular Weight | 56742.60 dalton |
| 1 microgram = | 17.623 pMoles |
| Molar Extinction coefficient | 92660 |
| A[280] of 1 mg/ml | 1.63 AU |

TABLE 2-continued

The analytical result of P243SV

| Analysis | Entire Protein |
|---|---|
| Isoelectric Point | 5.12 |
| Charge at pH 7 | −13.51 |

TABLE 3

The analytical result of P23WU1

| Analysis | Entire Protein |
|---|---|
| Length | 619 aa |
| Molecular Weight | 66895.60 |
| 1 microgram = | 14.949 pMoles |
| Molar Extinction coefficient | 128010 |
| A[280] of 1 mg/ml | 1.91 AU |
| Isoelectric Point | 5.62 |
| Charge at pH 7 | −6.67 |

These two alpha-amylases as purified in example 6 were further characterized according to the following methods.

AZCL-HE-Amylose Assay

Three microliters of alpha-amylase samples and 100 µl 0.2% AZCL-HE-amylose (Megazyme International Ireland Ltd.) at pH 4.3 were mixed separately in a Microtiter plate and placed on ice before reaction. The assay was initiated by transferring the Microtiter plate to an Eppendorf thermomixer, which was set to the assay temperature 40° C. Then 60 µl supernatant was transferred to a new microtiter plate. Optical Density at 595 nm ($OD_{595}$) was read as a measure of amylase activity. All reaction was done with duplicate and a buffer blind was included in the assay (instead of enzyme).

The adsorbances for P243SV and P23WU1 at $OD_{595}$ is 0.33 and 0.67, respectively, showing P243SV and P23WU1 have amylase activity.

pH Profile

Three microliters of enzyme samples and 40 µl 1% AZCL-HE-amylose in 100 µl B&R buffer (Britton-Robinson buffer: 0.1 M boric acid, 0.1 M acetic acid, and 0.1 M phosphoric acid) adjusted to pH-values 3.0, 4.0, 5.0, 6.0, 7.0, 8.0, 9.0, 10.0 and 11.0 with HCl or NaOH were mixed in an Microtiter plate and placed on ice before reaction. The assay was initiated by transferring the Microtiter plate to an Eppendorf thermomixer, which was set to the assay temperature 50° C. Then 60 µl supernatant was transferred to a new microtiter plate. $OD_{595}$ was read as a measure of amylase activity. All reaction was done with duplicate and a buffer blind was included in the assay (instead of enzyme).

Both alpha-amylases are acidic amylases and their optimal pH is pH4.0 as shown in table 4.

TABLE 4 pH profile of the alpha-amylases

| | pH | | | | | | | | | |
|---|---|---|---|---|---|---|---|---|---|---|
| | 2 | 3 | 4 | 5 | 6 | 7 | 8 | 9 | 10 | 11 |
| P243SV | 0.14 | 0.15 | 0.50 | 0.19 | 0.14 | 0.14 | 0.15 | 0.14 | 0.16 | 0.16 |
| P23WU1 | 0.11 | 0.20 | 0.77 | 0.73 | 0.66 | 0.68 | 0.64 | 0.36 | 0.14 | 0.11 | pH Stability

Twenty microliters of enzyme were added into 100 μl buffer (100 mM Na-acetate) at pH4.0, incubated at 37° C. for 0, 10, 30, 60 and 120 mins. The enzyme was added into 40 μl 1% AZCL-HE-amylose in water at 37° C. for 20 min, 60 μl taken for $OD_{595}$.

Both alpha-amylases are stable at pH4.0 as shown in table 5.

TABLE 5 pH stability of the alpha-amylases

| | Time (mins) | | | | |
|---|---|---|---|---|---|
| | 0 | 10 | 30 | 60 | 120 |
| P243SV | 0.56 | 0.85 | 0.67 | 0.63 | 0.60 |
| P23WU1 | 1.34 | 1.54 | 1.34 | 1.46 | 1.47 |

Temperature Profile

Three microliters of enzyme was added into 100 μl buffer (50 mM NaAc) at pH 4.3 containing 0.2% AZCL-HE-amylose, incubating for 20 mins and 60 μl supernatant was taken for $OD_{595}$.

P23WU1 shows higher optimal temperature (60° C.) than P243SV (40° C.) as shown in table 6.

TABLE 6

Temperature profile of the alpha-amylases

| | Temperature (° C.) | | | | | | |
|---|---|---|---|---|---|---|---|
| | 30 | 40 | 50 | 60 | 70 | 80 | 90 |
| P243SV | 0.30 | 0.33 | 0.14 | 0.10 | 0.10 | 0.08 | 0.09 |
| P23WU1 | 0.57 | 0.67 | 0.81 | 0.86 | 0.21 | 0.15 | 0.14 |

Temperature Stability

Three microliters of enzyme samples were added into 100 μl 50 mM NaAc at pH4.3 and incubated at 50° C. (P243SV) and 65° C. (P23WU1) for 0, 10, 30, 60 and 120 mins, and then they were put on ice at each time point. Forty microliters of 1% AZCL-HE-amylose in water was added at 37° C. for 20 mins, 60 μl taken for $OD_{595}$.

P243SV is more stable at 50° C., and P23WU1 is relatively stable at high temperature (65° C.), as shown in table 7.

TABLE 7

Temperature stabiltiy of the alpha-amylases

| | Time (mins) | | | | |
|---|---|---|---|---|---|
| | 0 | 10 | 30 | 60 | 120 |
| P243SV (50° C.) | 0.86 | 0.82 | 0.78 | 0.75 | 0.45 |
| P23WU1 (65° C.) | 0.74 | 0.58 | 0.42 | 0.27 | 0.13 |

Example 8: Simultaneous Saccharification and Fermentation (SSF) Performance of Recombinant *Penicillium oxalicum* Alpha-Amylase The SSF performance of purified *Penicillium oxalicum* alpha-amylase (P243SV or P23WU1) was tested at different enzyme doses in combination with a constant dose (equivalent to 0.56 AGU/gDS) of purified *Talaromyces emersonii* glucoamylase (disclosed in international publication WO 99/28448 as SEQ ID NO: 7) or in combination with a blend of *Talaromyces emersonii* glucoamylase and *Trametes Cingulata* glucoamylase (disclosed in international publication WO 2006/069289 as SEQ ID NO:2). *Talaromyces emersonii* glucoamylase and *Trametes Cingulata* glucoamylase were both expressed in *Aspergillus Niger*.

Fermentation was run under the following conditions:

Substrate: Industrially liquefied corn mash 33.9% DS (% w/w)

Temperature: 32° C.

Initial pH: 5.0

Alpha-amylase dose: *Penicillium oxalicum* alpha-amylase (obtained by Example 6) at 3 and 10 μg Enzyme Protein/g Dry Solid (μg EP/g DS).

Experiment A, *Penicillium oxalicum* alpha-amylases were compared to a purified sample of the *Talaromyces emersonii* glucoamylase dosed at same dosages. The dose of *Talaromyces emersonii* glucoamylase is equivalent to an industry relevant 0.56 AGU/gDS.

Experiment B, *Penicillium oxalicum* alpha-amylases were compared to a blend of commercial *Talaromyces emersonii* glucoamylase and *Trametes Cingulata* glucoamylase. The total glucoamylase dose is equivalent to an industry relevant 0.56 AGU/gDS.

Fermentation

The substrate for SSF was sampled after the liquefaction step in an ethanol facility. The ground corn was slurried with backset and other recycled water and adjusted its dry substance to approximately 33.9% (w/w), and it was then sent into liquefaction at 85° C. and pH 5.8. Before lab fermentations, 1000 ppm urea as nitrogen source and 3 ppm penicillin for bacterial control were added; the pH was then adjusted to 5.0 with $H_2SO_4$. Aliquots of substrate corresponding to about 5 g mash were transferred to 15 ml centrifuge tubes—with a hole drilled at the top for $CO_2$ release. Enzymes and yeast (30 million cells/ml) were added and the tubes were placed in a water bath without stirring at 32° C. Samples were analyzed in High Performance Liquid Chromatography (HPLC) for determination of the carbohydrate and ethanol concentrations.

The ethanol produced during fermentation is given in tables 8 and 9.

TABLE 8

Ethanol (g/L) produced during SSF with added *Penicillium oxalicum* alpha-amylase (P243SV or P23WU1) was tested at different enzyme doses in combination with *Talaromyces emersonii* glucoamylase) at 0.56 AGU/gDS as compared to *Talaromyces emersonii* glucoamylase alone, Experiment A

|  | Enzyme dose (μgEP/gDS) | |
|---|---|---|
|  | 3 | 10 |
| No alpha-amylase | 126.3 | |
| *Penicillium oxalicum* - P243SV | 125.6 | 126.0 |
| *Penicillium oxalicum* - P23WU1 | 129.0 | 129.8 |

TABLE 9

Ethanol (g/L) produced during SSF with added *Penicillium oxalicum* alpha-amylase (P23WU1) was tested at different enzyme doses in combination with a blend of *Talaromyces emersonii* glucoamylase and *Trametes Cingulata* glucoamylase at 0.56 AGU/gDS as compared to the glucoamylase blend alone, Experiment B

|  | Enzyme dose (μgEP/gDS) | |
|---|---|---|
|  | 3 | 10 |
| No alpha-amylase | 120.8 | |
| *Penicillium oxalicum* - P23WU1 | 122.6 | 123.6 |

Example 9: The Effect of the *Penicillium oxalicum* Alpha-Amylase on the Volume of the Bread Mini rolls were made of 12 g KOLIBRI™ flour (Meneba, Rotterdam, the Netherlands) according to a straight dough procedure with the addition of 56% water, 4.5% yeast, 1.5% sucrose, 1.5% salt and 40 ppm ascorbic acid based on the flour. Dough was supplemented with different dosages of enzymes according to table 10 below. All ingredients were mixed in a mini mixer (NS1-33R, National MFG Co., Lincoln, Nebr., United states) for 3.5 min at speed 3. After mixing the dough was shaped and placed in a round aluminum form (diameter 90 mm and side height 15 mm). After 55 min proofing at 32° C. and 86% Relative humidity (RH), the dough was baked at 230° C. for 17 min.

TABLE 10

| | Enzyme dosages | | | | | | |
|---|---|---|---|---|---|---|---|
| | 1 | 2 | 3 | 4 | 5 | 6 | 7 |
| P23WU1 (mg enzyme protein/kg flour) | | 0.33 | 1 | 3 | | | |
| P243SV (mg enzyme protein/kg flour) | | | | | 0.33 | 1 | 3 |

The effect of the enzyme on the volume of the breads was evaluated by a water displacement method, i.e., measuring the amount of water displaced by the bread at room temperature. A beaker containing water was put on a balance, which was then adjusted to 0.000 g. The bread was impregnated with paraffin at 80° C. for 3 second, allowed to cool for 10 second, and then immersed into the water in the beaker by pressure. The mass of the displaced water (gram), or the pressure applied, was read from the balance (gram). The mass of the displaced water corresponded to the volume of the bread (ml).

The bread was weighted on a balance and the specific volume was calculated by dividing the volume of bread (from water displacement method)) by the weight of bread (determined by weighing bread). A specific volume index was calculated by setting the specific volume of the control bread to 100% and calculating the specific volume of the enzyme treated bread relative to the control (no enzyme).

The effect of amylase P23WU1 and amylase P243SV on volume of mini rolls can be seen in table 2 below.

TABLE 2

Volume of rolls with different amylases

| Enzyme | specific volume (ml/g) | specific volume index (%) |
|---|---|---|
| Control (no enzyme) | 2.993 | 100 |
| P23WU1 (0.33 mg/kg) | 3.138 | 105 |
| P23WU1 (1 mg/kg) | 3.055 | 102 |
| P23WU1 (3 mg/kg) | 3.107 | 104 |
| P243SV (0.33 mg/kg) | 3.036 | 101 |
| P243SV (1 mg/kg) | 3.035 | 101 |
| P243SV (3 mg/kg) | 2.924 | 98 |

The amylase P23WU1 was able to improve the volume of the bread at 0.33 mg enzyme protein/kg flour, 1 mg enzyme protein/kg flour, and 3 mg enzyme protein/kg flour, respectively. The amylase P243SV was able to improve the volume of the bread at 0.33 mg enzyme protein/kg flour and 1 mg enzyme protein/kg flour, respectively.

The present invention is further described by the following numbered paragraphs:

[1] An isolated polypeptide having alpha-amylase activity, selected from the group consisting of:

(a) a polypeptide having at least 80%, e.g., at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 4; or a polypeptide having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2;

(b) a polypeptide encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 3, or the mature polypeptide coding sequence of SEQ ID NO: 1, (ii) the cDNA sequences thereof, or (iii) the full-length complement of (i) or (ii);

(c) a polypeptide encoded by a polynucleotide having at least 80%, e.g., at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 3 or the cDNA sequence thereof; or a polypeptide encoded by a polynucleotide having at least 65%, e.g., at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1 or the cDNA sequence thereof;

(d) a variant of the mature polypeptide of SEQ ID NO: 4 or the mature polypeptide of SEQ ID NO: 2 comprising a substitution, deletion, and/or insertion at one or more positions; and (e) a fragment of the polypeptide of (a), (b), (c), or (d) that has alpha-amylase activity.

[2] The polypeptide of paragraph 1, having at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 4; or at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2.

[3] The polypeptide of paragraph 1 or 2, which is encoded by a polynucleotide that hybridizes under low stringency conditions, low-medium stringency conditions, medium stringency conditions, medium-high stringency conditions, high stringency conditions, or very high stringency conditions with (i) the mature polypeptide coding sequence of SEQ ID NO: 3 or the mature polypeptide coding sequence of SEQ ID NO: 1, (ii) the cDNA sequence thereof, or (iii) the full-length complement of (i) or (ii).

[4] The polypeptide of any of paragraphs 1-3, which is encoded by a polynucleotide having at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 3 or the cDNA sequence thereof; or which is encoded by a polynucleotide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1 or the cDNA sequence thereof.

[5] The polypeptide of any of paragraphs 1-4, comprising or consisting of SEQ ID NO: 4, or SEQ ID NO: 2, the mature polypeptide of SEQ ID NO: 4, or the mature polypeptide of SEQ ID NO: 2.

[6] The polypeptide of paragraph 5, wherein the mature polypeptide is amino acids 21 to 619 of SEQ ID NO: 4, or amino acids 26 to 505 of SEQ ID NO: 2.

[7] The polypeptide of any of paragraphs 1-4, which is a variant of the mature polypeptide of SEQ ID NO: 4 or the mature polypeptide of SEQ ID NO: 2, comprising a substitution, deletion, and/or insertion at one or more positions; or which is a fragment of SEQ ID NO: 2 or SEQ ID NO: 4, wherein the fragment has alpha-amylase activity.

[8] The polypeptide of any of paragraphs 1-7, which is stable at 10° C.-100° C., preferably 20° C.-80° C., more preferably 30° C.-70° C.

[9] The polypeptide of any of paragraphs 1-8, which is a fragment of the polypeptide of SEQ ID NO: 4, or SEQ ID NO: 2, having alpha-amylase activity.

[10] An isolated polypeptide comprising a catalytic domain selected from the group consisting of:
(a) a catalytic domain having at least 80% sequence identity to amino acids 21 to 493 of SEQ ID NO: 4, or at least 65% sequence identity to amino acids 26 to 503 of SEQ ID NO: 2;
(b) a catalytic domain encoded by a polynucleotide that hybridizes under low, medium, medium-high, high, or very high stringency conditions with nucleotides 61 to 1973 of SEQ ID NO: 3, or nucleotides 76 to 1578 of SEQ ID NO: 1, (ii) the cDNA sequence thereof, or (iii) the full-length complement of (i) or (ii);
(c) a catalytic domain encoded by a polynucleotide having at least 80% sequence identity to nucleotides 61 to 1973 of SEQ ID NO: 3, or at least 65% sequence identity to nucleotides 76 to 1578 of SEQ ID NO: 1;
(d) a variant of amino acids 21 to 493 of SEQ ID NO: 4 or amino acids 26 to 503 of SEQ ID NO: 2, comprising a substitution, deletion, and/or insertion at one or more positions; and
(e) a fragment of the catalytic domain of (a), (b), (c), or (d) that has alpha-amylase activity.

[11] The polypeptide of paragraph 10, further comprising a carbohydrate binding domain.

[12] An isolated polypeptide comprising a carbohydrate binding domain, wherein the binding domain is selected from the group consisting of:
(a) a carbohydrate binding domain having at least 80% sequence identity to amino acids 511 to 619 of SEQ ID NO: 4;
(b) a carbohydrate binding domain encoded by a polynucleotide that hybridizes under low, medium, medium-high, high, or very high stringency conditions with (i) nucleotides 2025 to 2351 of SEQ ID NO: 3, (ii) the cDNA sequence thereof, or (iii) the full-length complement of (i) or (ii);
(c) a carbohydrate binding domain encoded by a polynucleotide having at least 80% sequence identity to nucleotides 2025 to 2351 of SEQ ID NO: 3 or the cDNA sequence thereof;
(d) a variant of amino acids 511 to 619 of SEQ ID NO: 4 comprising a substitution, deletion, and/or insertion at one or more positions; and
(e) a fragment of (a), (b), (c), (d) or (e) that has carbohydrate binding activity.

[13] The polypeptide of paragraph 12, wherein the carbohydrate binding domain is operably linked to a catalytic domain.

[14] The polypeptide of paragraph 13, wherein the catalytic domain is obtained from amylase.

[15] The polypeptide of paragraph 14, wherein the catalytic domain is obtained from alpha-amylase.

[16] The polypeptide of paragraph 15, wherein the catalytic domain is obtained from acid alpha-amylase.

[17] A whole broth formulation or cell culture composition comprising the polypeptide of any of paragraphs 1-16.

[18] A composition comprising the polypeptide of any of paragraphs 1-16 and an enzyme selected from the group consisting of: a fungal alpha-amylase (EC 3.2.1.1), a beta-amylase (E.C. 3.2.1.2), a glucoamylase (E.C.3.2.1.3), a pullulanases (E.C. 3.2.1.41), a phytase (E.C.3.1.2.28) and a protease (E.C. 3.4.).

[19] An isolated polynucleotide encoding the polypeptide of any of paragraphs 1-16.

[20] A nucleic acid construct or expression vector comprising the polynucleotide of paragraph 19 operably linked to one or more control sequences that direct the production of the polypeptide in an expression host.

[21] A recombinant host cell comprising the polynucleotide of paragraph 19 operably linked to one or more control sequences that direct the production of the polypeptide.

[22] A method of producing the polypeptide of any of paragraphs 1-16, comprising: cultivating a cell, which in its wild-type form produces the polypeptide, under conditions conducive for production of the polypeptide.

[23] A method of paragraph 22, further comprising recovering the polypeptide.

[24] A method of producing a polypeptide having alpha-amylase activity, comprising: cultivating the host cell of paragraph 21 under conditions conducive for production of the polypeptide.

[25] A method of paragraph 24, further comprising recovering the polypeptide.

[26] A transgenic plant, plant part or plant cell transformed with a polynucleotide encoding the polypeptide of any of paragraphs 1-16.

[27] A method of producing a polypeptide having alpha-amylase activity, comprising: cultivating the transgenic plant or plant cell of paragraph 26 under conditions conducive for production of the polypeptide.

[28] A method of paragraph 27, further comprising recovering the polypeptide.

[29] A method of producing a mutant of a parent cell, comprising inactivating a polynucleotide encoding the polypeptide of any of paragraphs 1-16, which results in the mutant producing less of the polypeptide than the parent cell.

[30] A mutant cell produced by the method of paragraph 29.

[31] The mutant cell of paragraph 30, further comprising a gene encoding a native or heterologous protein.

[32] A method of producing a protein, comprising:
cultivating the mutant cell of paragraph 30 or 31 under conditions conducive for production of the protein.

[33] A method of paragraph 32, further comprising recovering the polypeptide.

[34] A double-stranded inhibitory RNA (dsRNA) molecule comprising a subsequence of the polynucleotide of paragraph 19, wherein optionally the dsRNA is an siRNA or an miRNA molecule.

[35] The double-stranded inhibitory RNA (dsRNA) molecule of paragraph 34, which is about 15, 16, 17, 18, 19, 20, 21, 22, 23, 24, 25 or more duplex nucleotides in length.

[36] A method of inhibiting the expression of a polypeptide having alpha-amylase activity in a cell, comprising administering to the cell or expressing in the cell the double-stranded inhibitory RNA (dsRNA) molecule of paragraph 34 or 35.

[37] A cell produced by the method of paragraph 36.

[38] The cell of paragraph 37, further comprising a gene encoding a native or heterologous protein.

[39] A method of producing a protein, comprising:
cultivating the cell of paragraph 37 or 38 under conditions conducive for production of the protein.

[40] A method of paragraph 39, further comprising recovering the polypeptide.

[41] An isolated polynucleotide encoding a signal peptide comprising or consisting of amino acids 1 to 20 of SEQ ID NO: 4, or amino acids 1 to 25 of SEQ ID NO: 2.

[44] A nucleic acid construct or expression vector comprising a gene encoding a protein operably linked to the polynucleotide of paragraph 41, wherein the gene is foreign to the polynucleotide encoding the signal peptide.

[45] A recombinant host cell comprising a gene encoding a protein operably linked to the polynucleotide of paragraph 41, wherein the gene is foreign to the polynucleotide encoding the signal peptide.

[46] A method of producing a protein, comprising:
cultivating a recombinant host cell comprising a gene encoding a protein operably linked to the polynucleotide of paragraph 41, wherein the gene is foreign to the polynucleotide encoding the signal peptide, under conditions conducive for production of the protein.

[47] A method of paragraph 46, further comprising recovering the protein.

[48] Use of the polypeptide according to any of paragraphs 1-16, the whole broth formulation or cell culture composition according to paragraph 17 or the composition according to paragraph 18 for starch conversion.

[49] Use of the polypeptide according to any of paragraphs 1-16, the whole broth formulation or cell culture composition according to paragraph 17 or the composition according to paragraph 18 for starch modification in the paper and pulp industry.

[50] Use of the polypeptide according to any of paragraphs 1-16, the whole broth formulation or cell culture composition according to paragraph 17 or the composition according to paragraph 18 for starch liquefaction and/or saccharification.

[51] Use of the polypeptide according to any of paragraphs 1-16, the whole broth formulation or cell culture composition according to paragraph 17 or the composition according to paragraph 18 for textile washing.

[52] Use of the polypeptide according to any of paragraphs 1-16, the whole broth formulation or cell culture composition according to paragraph 17 or the composition according to paragraph 18 for textile desizing.

[53] Use of the polypeptide according to any of paragraphs 1-16, the whole broth formulation or cell culture composition according to paragraph 17 or the composition according to paragraph 18 for brewing.

[54] Use of the polypeptide according to any of paragraphs 1-16, the whole broth formulation or cell culture composition according to paragraph 17 or the composition according to paragraph 18 for ethanol production.

[55] Use according to paragraph 54 for production of ethanol in a process comprising hydrolyzing starch.

[56] Use of the polypeptide according to any of paragraphs 1-16, the whole broth formulation or cell culture composition according to paragraph 17 or the composition according to paragraph 18 for baking.

[57] Use according to paragraph 56 for the improvement of the volume of a bread.

[58] A method for converting starch, preferably gelatinized starch, wherein a polypeptide according to any of paragraphs 1-16, the whole broth formulation or cell culture composition according to paragraph 17 or the composition according to paragraph 18 is added.

[59] A method for modificating starch in the paper and pulp industry, wherein a polypeptide according to any of paragraphs 1-16, the whole broth formulation or cell culture composition according to paragraph 17 or the composition according to paragraph 18 is added.

[60] A method for liquefying and/or saccharifying starch, wherein a polypeptide according to any of paragraphs 1-16, the whole broth formulation or cell culture composition according to paragraph 17 or the composition according to paragraph 18 is added.

[61] A method for washing textile, wherein a polypeptide according to any of paragraphs 1-16, the whole broth formulation or cell culture composition according to paragraph 17 or the composition according to paragraph 18 is added.

[62] A method for desizing textile, wherein a polypeptide according to any of paragraphs 1-16, the whole broth formulation or cell culture composition according to paragraph 17 or the composition according to paragraph 18 is added.

[63] A method for brewing, wherein a polypeptide according to any of paragraphs 1-16, the whole broth formulation or cell culture composition according to paragraph 17 or the composition according to paragraph 18 is added.

[64] A method for producing ethanol, wherein a polypeptide according to any of paragraphs 1-16, the whole broth formulation or cell culture composition according to paragraph 17 or the composition according to paragraph 18 is added.

[65] A method according to paragraph 64, wherein the ethanol is produced in a process comprising hydrolyzing starch.

[66] A method for baking, wherein a polypeptide according to any of paragraphs 1-16, the whole broth formulation or cell culture composition according to paragraph 17 or the composition according to paragraph 18 is added.

[67] A method according to paragraph 66, wherein a polypeptide according to any of paragraphs 1-16, the whole broth formulation or cell culture composition according to paragraph 17 or the composition according to paragraph 18 is added to dough.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A nucleic acid construct or expression vector comprising a polynucleotide encoding a polypeptide having alpha-amylase activity and one or more heterologous control sequences that direct production of the polypeptide in an expression host, wherein the polynucleotide is operably linked to the one or more heterologous control sequences that direct production of the polypeptide in an expression host, and wherein the amino acid sequence of the polypeptide has at least 90% sequence identity to the sequence of amino acids 21 to 619 of SEQ ID NO:4.

2. The nucleic acid construct or expression vector of claim 1, wherein the amino acid sequence of the polypeptide has at least 95% sequence identity to the sequence of amino acids 21 to 619 of SEQ ID NO:4.

3. The nucleic acid construct or expression vector of claim 1, wherein the amino acid sequence of the polypeptide has at least 97% sequence identity to the sequence of amino acids 21 to 619 of SEQ ID NO:4.

4. The nucleic acid construct or expression vector of claim 1, wherein the amino acid sequence of the polypeptide has at least 99% sequence identity to the sequence of amino acids 21 to 619 of SEQ ID NO:4.

5. The nucleic acid construct or expression vector of claim 1, wherein the polypeptide comprises or consists of the amino acid sequence of SEQ ID NO: 4, or the sequence of amino acids 21 to 619 of SEQ ID NO: 4.

6. The nucleic acid construct or expression vector of claim 1, wherein the polypeptide comprises a catalytic domain wherein the catalytic domain has alpha-amylase activity and wherein the amino acid sequence of the catalytic domain has at least 95% sequence identity to the sequence of amino acids 21 to 493 of SEQ ID NO: 4.

7. The nucleic acid construct or expression vector of claim 1, wherein the polypeptide comprises a carbohydrate binding domain, wherein the binding domain has carbohydrate binding activity and wherein the amino acid sequence of the binding domain has at least 95% sequence identity to the sequence of amino acids 511 to 619 of SEQ ID NO: 4.

8. An isolated host cell transformed with the nucleic acid construct or expression vector of claim 1.

9. The host cell of claim 8, wherein the host cell is a yeast host cell.

10. The host cell of claim 9, wherein the yeast host cell is selected from the group consisting of a *Candida*, *Hansenula*, *Kluyveromyces*, *Pichia*, *Saccharomyces*, *Schizosaccharomyces*, and *Yarrowia* cell.

11. The host cell of claim 10, wherein the *Kluyveromyces* cell is a *Kluyveromyces lactis* cell.

12. The host cell of claim 10, wherein the *Saccharomyces* cell is selected from the group consisting of *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, and *Saccharomyces oviformis*.

13. The host cell of claim 10, wherein the *Yarrowia* cell is a *Yarrowia lipolytica* cell.

14. A method of producing a polypeptide having alpha-amylase activity, comprising:

(a) cultivating an isolated host cell transformed with the nucleic acid construct or expression vector of claim 1 under conditions conducive for production of the polypeptide; and optionally
(b) recovering the polypeptide.

* * * * *